US011547282B2

(12) United States Patent
Weise et al.

(10) Patent No.: US 11,547,282 B2
(45) Date of Patent: Jan. 10, 2023

(54) ARRANGEMENT FOR THE STERILE HANDLING OF NON-STERILE UNITS IN A STERILE ENVIRONMENT

(71) Applicant: avateramedical GmbH, Jena (DE)

(72) Inventors: Fabian Weise, Berlin (DE); Martin Lück, Esslingen (DE); Hartmut Vogelsang, Oberweser (DE); Peter Preuss, Jena (DE)

(73) Assignee: avateramedical GmbH

( * ) Notice: Subject to any disclaimer, the term of this patent is extended or adjusted under 35 U.S.C. 154(b) by 723 days.

(21) Appl. No.: 16/303,740

(22) PCT Filed: May 23, 2017

(86) PCT No.: PCT/EP2017/062379
§ 371 (c)(1),
(2) Date: Nov. 21, 2018

(87) PCT Pub. No.: WO2017/202831
PCT Pub. Date: Nov. 30, 2017

(65) Prior Publication Data
US 2020/0275827 A1    Sep. 3, 2020

(30) Foreign Application Priority Data
May 25, 2016    (DE) .......................... 102016109601.6

(51) Int. Cl.
*A61B 1/00* (2006.01)
*H01R 13/453* (2006.01)
(Continued)

(52) U.S. Cl.
CPC ...... *A61B 1/00142* (2013.01); *A61B 1/00114* (2013.01); *A61B 1/00117* (2013.01);
(Continued)

(58) Field of Classification Search
CPC .... H01H 1/5866; H01H 1/38; A61B 1/00124; A61B 1/00142; A61B 1/00114;
(Continued)

(56) References Cited

U.S. PATENT DOCUMENTS 4,176,897 A * 12/1979 Cameron ............... H01R 13/44
439/138
4,217,019 A * 8/1980 Cameron ............... H01R 13/44
439/138
(Continued)

FOREIGN PATENT DOCUMENTS

CN    104518351 A    4/2015
CN    104662744 A    5/2015
(Continued)

OTHER PUBLICATIONS

Russian Patent Office, Office Action re Corresponding Application No. 2018145724, dated Aug. 25, 2020, 12 pages, Russia.

*Primary Examiner* — Anh Tuan T Nguyen
*Assistant Examiner* — Shankar Raj Ghimire
(74) *Attorney, Agent, or Firm* — McGarry Bair PC

(57) ABSTRACT

An arrangement for the sterile handling of a non-sterile endoscope in a sterile environment comprises a sterile endoscope sheath for accommodating the endoscope and a cable via which the endoscope is connectable to a control unit, the arrangement further comprising a sterile cable sheath for accommodating at least a portion of the cable, wherein the endoscope sheath comprises a first sterile lock comprising at least one first sterile flap which in the closed state shields the endoscope arranged in the endoscope sheath in a sterile manner. The cable sheath comprises a second sterile lock having a second sterile flap which in a closed state shields the cable arranged in the cable sheath and/or a plug connector present on the arranged cable in a sterile manner. When connecting the cable or the plug connector to
(Continued)

the endoscope, a movement of the first sterile flap from the closed state into an open state takes place and a movement of the second sterile flap from the closed state into an open state takes place so that a direct coupling of the cable to the endoscope or of the plug connector connected to the cable to a complementary plug connector of the endoscope is possible.

16 Claims, 18 Drawing Sheets

(51) Int. Cl.
*A61B 34/35* (2016.01)
*A61B 34/00* (2016.01)
*A61B 1/07* (2006.01)
*A61B 34/30* (2016.01)

(52) U.S. Cl.
CPC ............... *A61B 1/07* (2013.01); *A61B 34/35* (2016.02); *A61B 34/74* (2016.02); *A61B 2034/301* (2016.02)

(58) Field of Classification Search
CPC ....... A61B 1/00117; A61B 1/07; A61B 34/35; A61B 34/74; A61B 2034/301; A61B 2017/00477; A61B 2090/0813; A61B 1/00121; A61B 46/10; H01R 13/4536; H01R 13/4538; H01R 13/5213; H01R 13/5224; H01R 2201/12; H01R 13/4534; H01R 13/447
USPC .................................. 439/141, 135; 340/656
See application file for complete search history.

(56) References Cited

U.S. PATENT DOCUMENTS

| | | | | |
|---|---|---|---|---|
| 4,345,808 A * | 8/1982 | Ingham | ................ | H01R 13/658 439/138 |
| 4,877,033 A * | 10/1989 | Seitz, Jr. | ................ | A61B 46/17 600/101 |
| 5,168,863 A * | 12/1992 | Kurtzer | ................ | A61B 1/00142 600/122 |
| 5,591,119 A * | 1/1997 | Adair | ................ | A61B 46/10 600/122 |
| 5,695,449 A * | 12/1997 | Moriyama | ................ | A61B 1/00142 600/122 |
| 5,792,045 A * | 8/1998 | Adair | ................ | A61B 1/00128 600/125 |
| 5,873,814 A * | 2/1999 | Adair | ................ | A61B 1/00042 600/109 |
| 5,876,328 A * | 3/1999 | Fox | ................ | A61B 46/10 600/122 |
| 5,924,977 A | 7/1999 | Yabe | | |
| 5,957,831 A * | 9/1999 | Adair | ................ | A61B 1/00142 600/101 |
| 5,980,450 A * | 11/1999 | Thompson | ................ | A61B 1/042 600/122 |
| 6,206,577 B1 * | 3/2001 | Hall, III | ................ | G02B 6/3825 439/138 |
| 6,594,971 B1 * | 7/2003 | Addy | ................ | B65D 75/32 53/433 |
| 7,918,674 B2 * | 4/2011 | Dufresne de Virel | ................ | H01R 13/5213 439/138 |
| 8,317,689 B1 * | 11/2012 | Remijan | ................ | A61B 1/042 600/125 |
| 8,910,637 B2 * | 12/2014 | Winer | ................ | A61B 46/00 128/854 |
| 9,629,680 B2 * | 4/2017 | Winer | ................ | A61B 46/00 |
| 11,103,321 B2 * | 8/2021 | Braun | ................ | A61B 34/35 |
| 2002/0133058 A1 * | 9/2002 | Calderwood | ...... | A61B 1/00142 600/122 |
| 2003/0192799 A1 * | 10/2003 | Addy | ................ | A61B 1/00142 206/439 |
| 2004/0127891 A1 * | 7/2004 | Humble | ................ | A61B 46/13 606/1 |
| 2005/0043770 A1 * | 2/2005 | Hine | ................ | H01R 13/5224 607/37 |
| 2005/0101838 A1 * | 5/2005 | Camillocci | ........ | A61B 1/00059 600/125 |
| 2005/0234295 A1 * | 10/2005 | Gomez | ................ | A61B 1/00142 600/127 |
| 2006/0161138 A1 * | 7/2006 | Orban, III | ................ | A61B 34/30 606/1 |
| 2007/0078304 A1 * | 4/2007 | Shimizu | ................ | A61B 1/00124 600/110 |
| 2007/0123798 A1 * | 5/2007 | Rahamimov | ...... | A61B 1/00135 600/564 |
| 2007/0185383 A1 * | 8/2007 | Mulhern | ................ | A61B 1/00142 600/101 |
| 2008/0231695 A1 * | 9/2008 | Favonio | ................ | A61B 1/00101 348/E7.085 |
| 2008/0300553 A1 * | 12/2008 | Irion | ................ | A61B 1/00039 604/263 |
| 2009/0024145 A1 * | 1/2009 | Meade | ................ | A61B 17/06114 606/144 |
| 2009/0215311 A1 | 8/2009 | Omori | | |
| 2009/0253962 A1 | 10/2009 | Fernandez et al. | | |
| 2010/0234733 A1 * | 9/2010 | Wahlheim | ............ | A61B 8/4281 600/459 |
| 2012/0010468 A1 * | 1/2012 | Afridi | ................ | A61B 1/00142 600/121 |
| 2013/0345503 A1 * | 12/2013 | Friedrich | ........... | A61B 1/00142 600/103 |
| 2014/0158141 A1 * | 6/2014 | Winer | ................ | A61B 46/10 128/854 |
| 2014/0160261 A1 * | 6/2014 | Miller | ................ | A61B 1/313 348/77 |
| 2014/0171740 A1 * | 6/2014 | Gestetner | ............ | A61B 1/0008 600/121 |
| 2015/0047647 A1 * | 2/2015 | Winer | ................ | A61B 46/00 128/854 |
| 2015/0090063 A1 | 4/2015 | Lantermann | | |
| 2015/0133960 A1 * | 5/2015 | Lohmeier | ............ | A61B 90/40 606/130 |
| 2015/0148818 A1 * | 5/2015 | Lohmeier | ............ | A61B 90/98 606/130 |
| 2015/0202009 A1 * | 7/2015 | Nussbaumer | ......... | A61B 46/27 128/856 |
| 2015/0362828 A1 * | 12/2015 | Patel | ................ | A61B 1/0661 348/75 |
| 2016/0000507 A1 * | 1/2016 | Neuberger | ............ | A61B 18/22 606/10 |
| 2016/0174821 A1 * | 6/2016 | Homze | ................ | A61B 1/00142 600/125 |
| 2016/0361122 A1 * | 12/2016 | Seeber | ................ | A61B 34/32 |
| 2016/0361128 A1 * | 12/2016 | Seeber | ................ | A61B 90/30 |
| 2017/0143404 A1 * | 5/2017 | Hancock | ................ | A61B 18/12 |
| 2017/0209027 A1 * | 7/2017 | Raj | ................ | A61B 1/00034 |
| 2017/0333147 A1 * | 11/2017 | Bernstein | ................ | A61B 34/30 |
| 2018/0310808 A1 * | 11/2018 | Laser | ................ | A61B 1/00142 |
| 2019/0167078 A1 * | 6/2019 | Fryer | ................ | A61B 1/00142 |
| 2020/0275827 A1 * | 9/2020 | Weise | ................ | A61B 34/74 |

FOREIGN PATENT DOCUMENTS

| | | |
|---|---|---|
| DE | 29905355 U1 | 7/1999 |
| DE | 102010022429 A1 | 12/2011 |
| DE | 102012008535 A1 | 10/2013 |
| JP | 5-28351 | 4/1993 |
| JP | 2002119517 A | 4/2002 |
| JP | 2002301029 A | 10/2002 |
| JP | 2016514562 A | 5/2016 |
| RU | 2435513 | 5/2010 |

(56) References Cited

FOREIGN PATENT DOCUMENTS

| | | | |
|---|---|---|---|
| WO | 2007113400 | A1 | 10/2007 |
| WO | 2012075989 | A1 | 6/2012 |
| WO | 2013183014 | A1 | 12/2013 |

\* cited by examiner

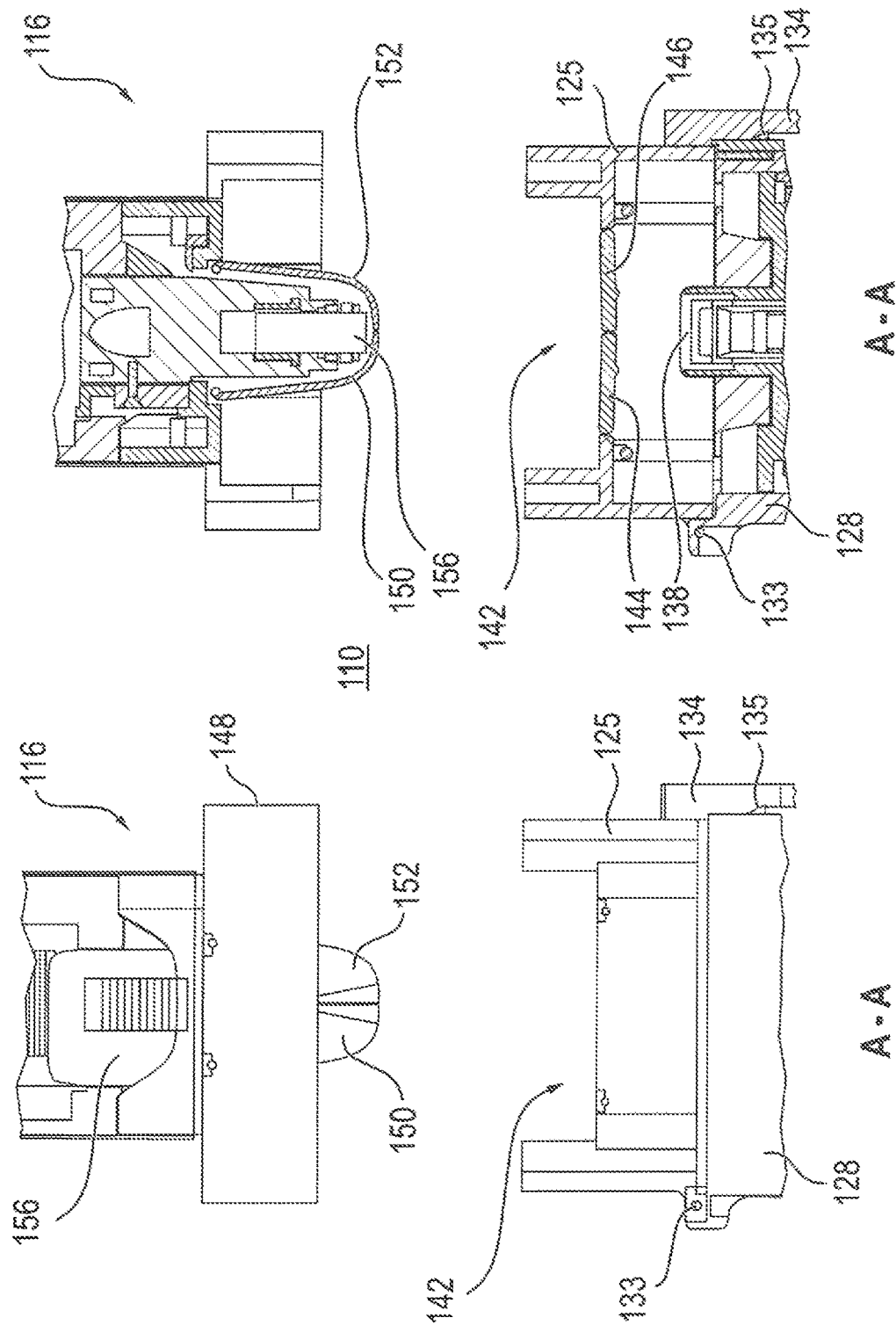

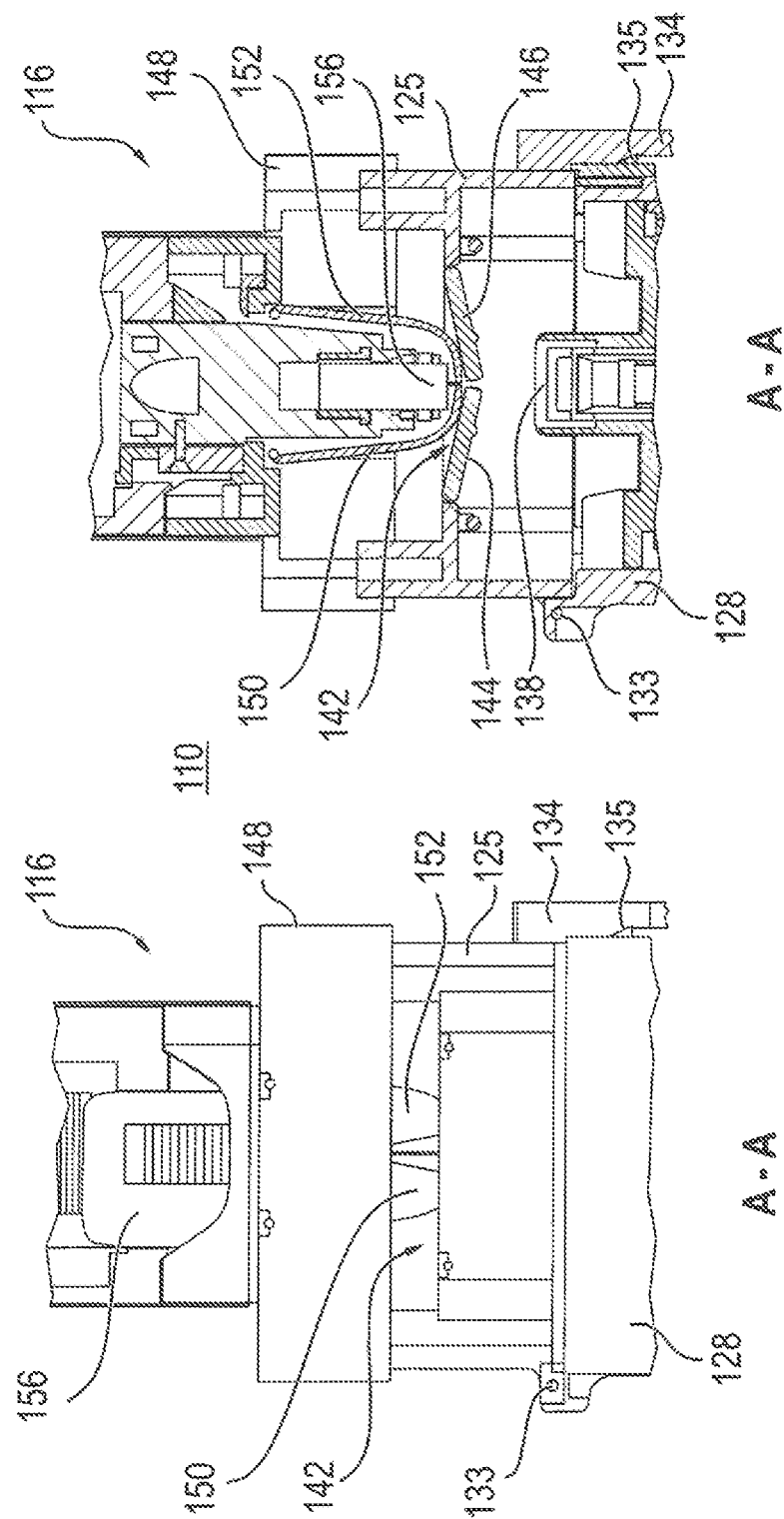

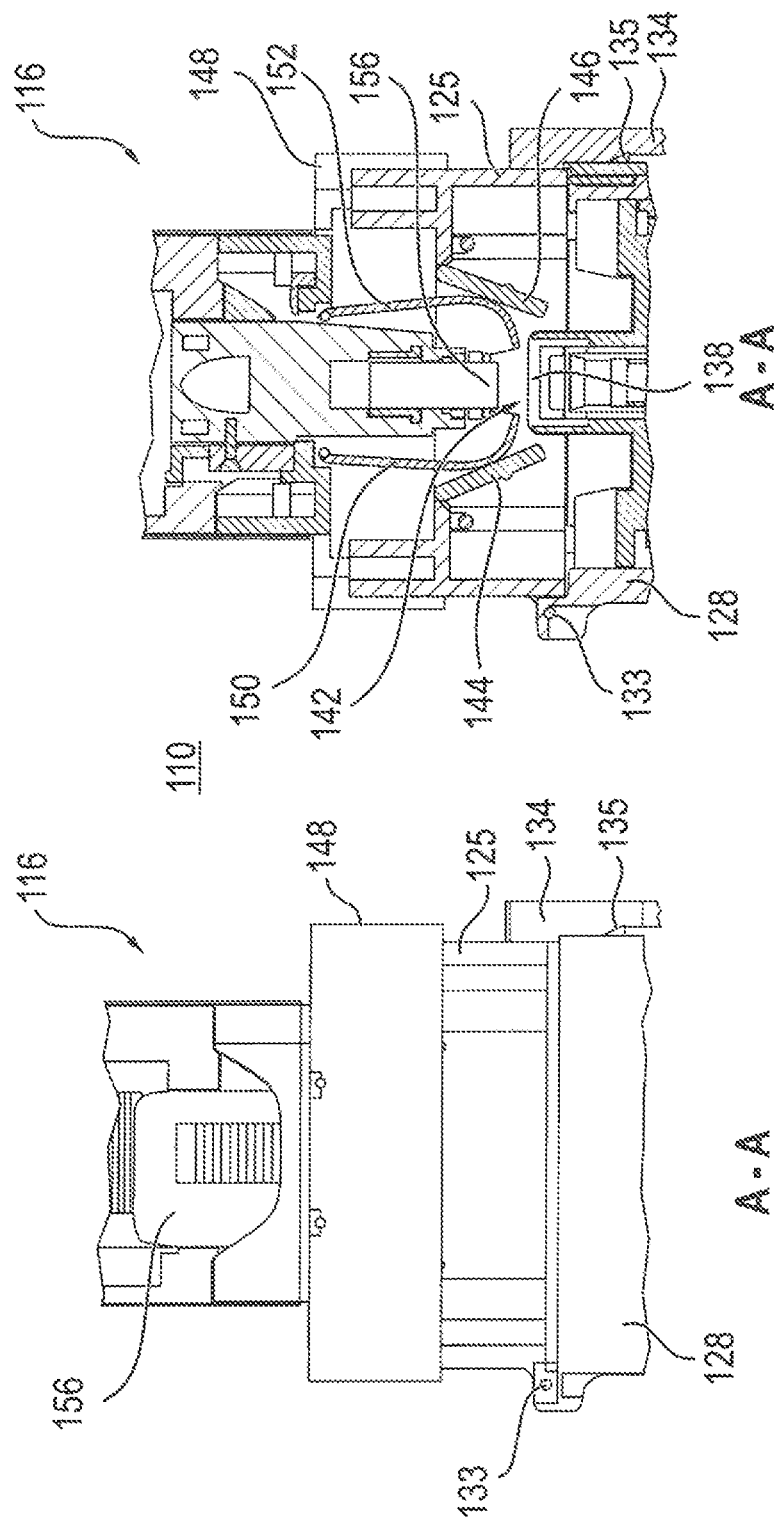

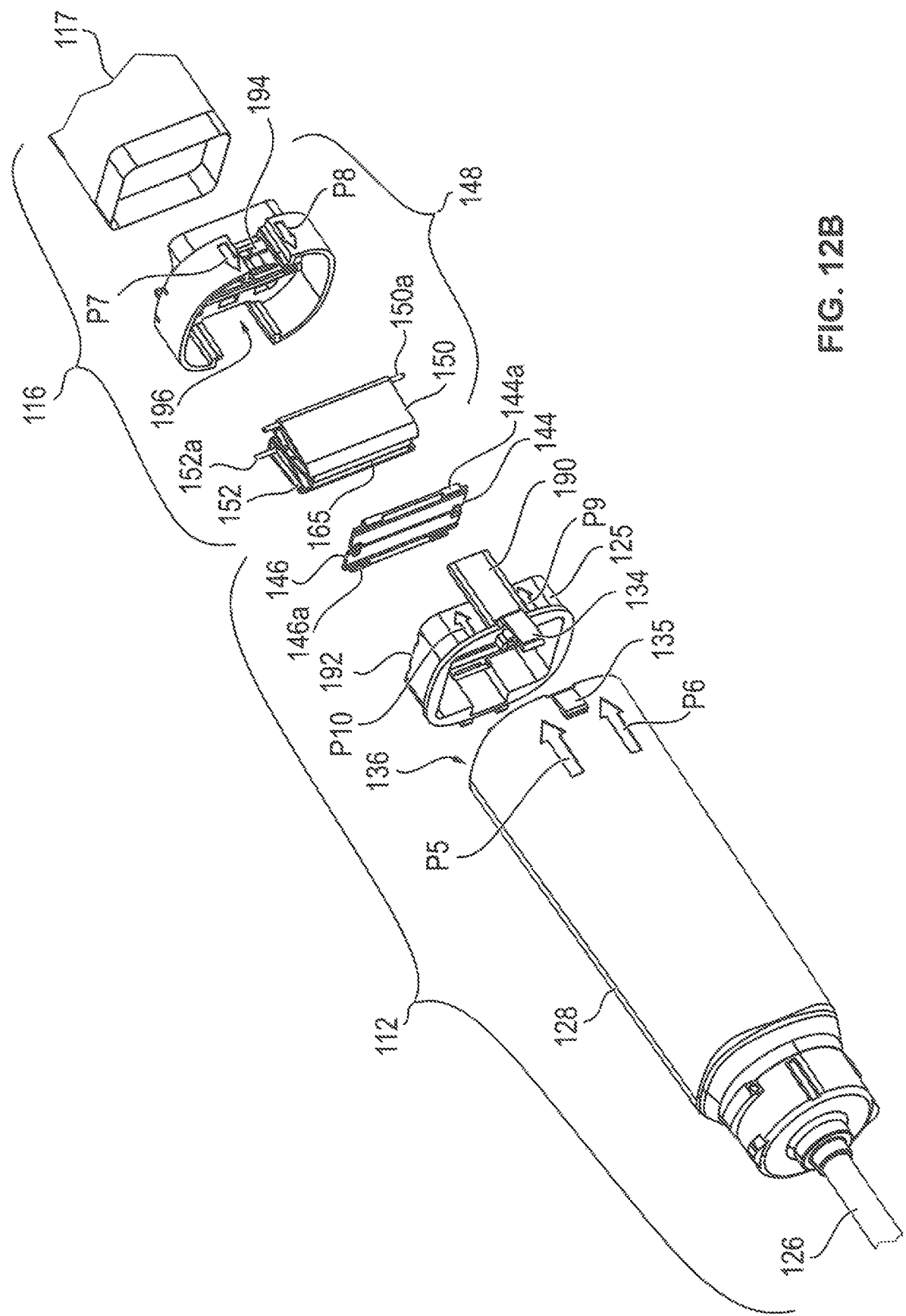

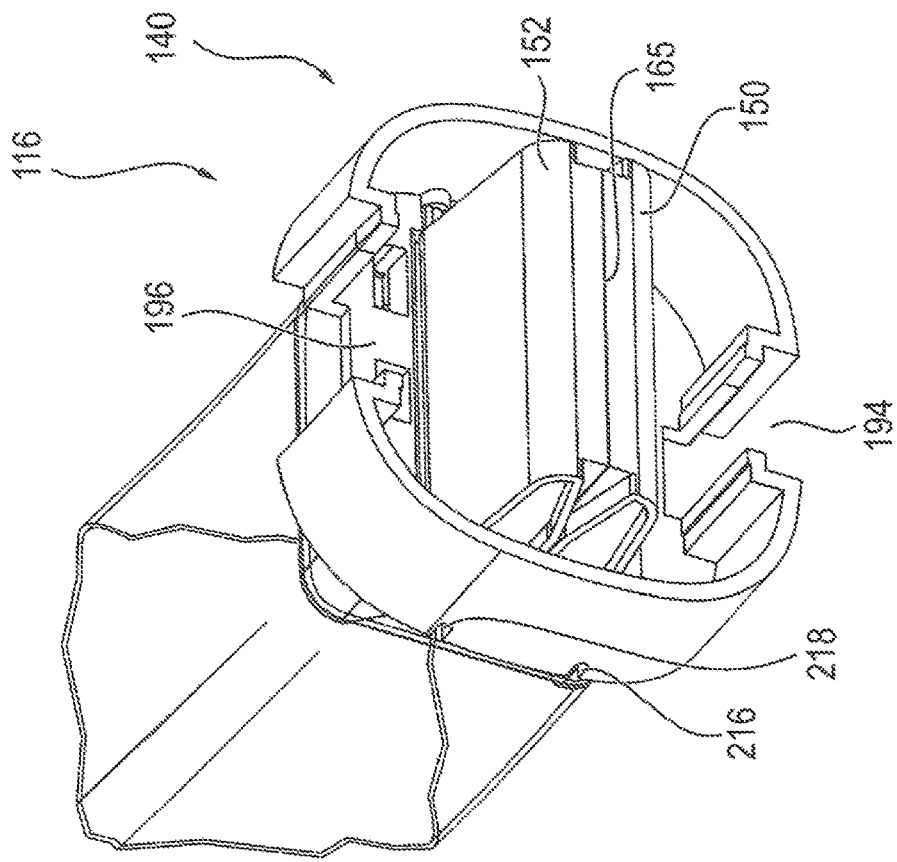
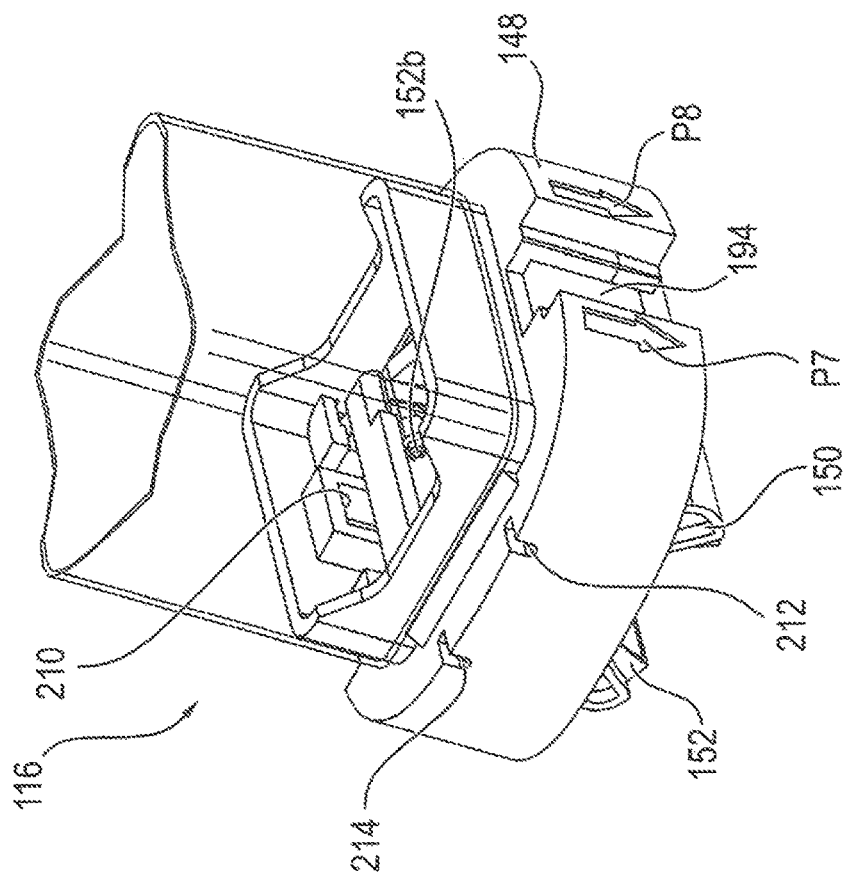
FIG. 15A
FIG. 15B

ARRANGEMENT FOR THE STERILE HANDLING OF NON-STERILE UNITS IN A STERILE ENVIRONMENT

CROSS-REFERENCES TO RELATED APPLICATIONS

This application is a National Phase application of International Application No. PCT/EP2017/062379, filed May 23, 2017, which claims the benefit of German Application DE 10 2016 109 601.6, filed on May 25, 2016, both which are incorporated herein in their entireties.

TECHNICAL FIELD

The invention relates to a first arrangement for the sterile handling of a non-sterile endoscope in a sterile environment. The arrangement comprises a sterile endoscope sheath for accommodating the endoscope, a cable via which the endoscope is connectable to a control unit, and a sterile cable sheath for accommodating at least a portion of the cable. Further, the invention relates to a second arrangement for establishing and disconnecting a plug connection between a first non-sterile plug connector and a second non-sterile plug connector that is complementary to the first plug connector in a sterile environment. This second arrangement comprises a first sterile sheath for accommodating at least the first plug connector and a second sterile sheath for accommodating at least the second plug connector.

BACKGROUND

The invention is based on the idea to use a non-sterile endoscope in a sterile environment, such as an operating room, without having to sterilize the endoscope. Basically, it would indeed also be possible to use sterile one-time endoscopes which are only used for one single operation, but this is not useful neither from an economical point of view nor from the view of a considerate dealing with resources. Together with the endoscope, also connecting cables between a control unit and the endoscope should not have to be sterilized prior to each and every use when used multiple times. For the use of non-sterile endoscopes in a sterile environment, a sheath for an endoscope is known from document DE 10 2010 022 429 A1, said sheath having two sheath parts which can be mechanically connected to each other in a disconnectable and fluid-tight manner. In this embodiment, a connecting cable for connection to the endoscope is firmly connected to the endoscope, while it is not provided that cables present in the protective tube are separated from the endoscope in the sterile environment.

From document WO 2012/075989 A1, a manually operated endoscope for medical purposes is known, which comprises a separate module-type unit and a transmission system. The unit is not sterile and can be inserted into a sterilized housing.

From document DE 10 2012 008 535 A1, a surgical robot system is known, in which a sterile endoscope is connected to a non-sterile manipulator arm. To this end, a sterile instrument adapter is provided between the manipulator arm and the endoscope.

These known solutions have the disadvantage that the endoscope cannot be separated from the connecting cable and replaced by another endoscope in the sterile area without jeopardizing the sterility in the sterile environment. Thus, in practice it is not possible to change the endoscope in the sterile area during a surgery. Should an endoscope have a defect and must be replaced during a surgery, or should, during a surgery, an inserted endoscope be replaced against another endoscope with other optical and/or geometric properties, then this second endoscope would have to be packed in a sterile manner together with a sterile cable already prior to the surgery and be exchanged for the first endoscope during the surgery. Alternatively, sterile endoscopes and/or sterile cables can also be exchanged for one another in the sterile environment. However, it is very expensive to sterilize endoscopes and cables prior to each use. For this, it is necessary that the endoscope is cleaned and autoclaved after each use. In the autoclave, the endoscope is subjected to steam at a temperature of about 140° C. and a pressure of several bars so that considerable thermal and mechanical demands have to be made on the endoscope so that it safely withstands the sterilization process in the autoclave.

Similar problems occur in the case of the connection of several plug connectors which are provided either directly on devices in sterile packs and/or on cable ends.

BRIEF DESCRIPTION

It is the object of the invention to specify an arrangement for the sterile handling of a non-sterile endoscope in a sterile environment as well as an arrangement for establishing and disconnecting a plug connection between a first non-sterile plug connector and a second non-sterile plug connector in a sterile environment, which arrangements enable the establishment and the disconnection of a connection between the endoscope and a cable or between two plug connectors without contaminating the sterile environment. In addition, a system for a robot-assisted surgery, in particular for a telerobot-assisted procedure within a sterile area is to be specified, in which the endoscope is positionable in the sterile area with the aid of a manipulator arm of a manipulator.

This object is solved by an arrangement for the sterile handling of a non-sterile endoscope in a sterile environment having the features of claim 1, by an arrangement for the robot-assisted surgery having the features of claim 14 as well as by an arrangement for establishing and disconnecting a plug connection between a first sterile plug connector and a second sterile plug connector in a sterile environment having the features of claim 15. Advantageous developments are specified in the dependent claims.

By an arrangement for the sterile handling of a non-sterile endoscope in a sterile environment having the features of claim 1, it is achieved that a direct connection between the non-sterile endoscope and the non-sterile cable or the non-sterile plug connector connected to the cable can be both established and disconnected in a reliable manner, without any risk that the sterile area will be contaminated. This is in particular achieved with the aid of the first sterile lock with the first sterile flap and the second sterile lock with the second sterile flap. As a result, both an easy exchange of an endoscope for another endoscope in the sterile environment and the re-connection of an endoscope already previously connected to the cable in the sterile environment is possible. This is in particular useful whenever several endoscopes with different optical and/or geometrical properties are employed during a medical treatment, in particular a surgery.

It is particularly advantageous when the second sterile lock is connectable to the cable or to the plug connector present on the cable via a disconnectable snap-in connection. As a result, an easy and joint handling during the establishment and the disconnection of a connection of the sterile lock and the cable or the plug connector present on the cable with the endoscope or with a plug connector present on the endoscope is possible. By means of the disconnectable snap-in connection, the sterile lock is thus easily connectable to the cable or to the plug connector present on the cable as well as after use again separable from the cable or the plug connector, respectively.

Further, it is advantageous when the endoscope sheath has an opening into which the endoscope is insertable, and when the opening of the endoscope sheath is closable in a sterile manner with the aid of a closing element, wherein the closing element preferably comprises the first sterile lock. The closing element can in particular be configured as a plate or cap closing the opening of the endoscope sheath. The closing element can be connected to the endoscope sheath via a film hinge and/or a snap-in connection. Between the opening of the endoscope sheath and the closing element, further a sealing area and/or at least one sealing element can be provided which seals the interface between the closing element and the opening of the endoscope sheath in a fluid-tight manner. As an alternative to the snap-in connection or the click connection, the closing element can also be connected to the remaining endoscope sheath via another suitable positive or non-positive connection. Preferably, the endoscope sheath comprises the closing element with the first sterile lock, the closing element and the remaining endoscope sheath being formed in one piece, preferably monolithically. In this context, in one piece means that the closing element and the remaining endoscope sheath are connected to form one component part, so that they can be handled jointly. The closing element and the remaining endoscope sheath may however have been produced separately and then be connected to one another. The connection may in particular be a non-positive connection, a material connection or a positive connection. Preferably, in the one-piece design, the closing element is connectable to the remaining endoscope sheath such that this connection is disconnectable in a non-destructive manner. In the case of a monolithically formed design, which is a specialty of the one-piece design, the closing element and the endoscope sheath are not separable in a non-destructive manner. Preferably, they are produced in an interconnected state, in particular by a casting procedure, in which a film hinge is formed between the closing element and the remaining endoscope sheath. The first sterile lock may however comprise further separately manufactured components parts. In the case of a monolithic design, the closing element and the endoscope sheath are thus preferably not separable from one another in a non-destructive manner.

Preferably, the cable is an electric cable with at least one electric conductor, an optical cable with at least one optical transmission path, a light guide cable with at least one optical transmission path or a hybrid cable with at least one electric conductor and at least one optical transmission path. The optical transmission path may in particular comprise at least one optical fiber. Preferably, the plug connector couples the at least one optical transmission path of the cable to at least one optical element of the endoscope. Alternatively or additionally, the plug connector can connect the at least one electric conductor of the cable to at least one electric connection of the endoscope. Via the plug connector, a simple connection between the endoscope and the cable is possible without special knowledge or skills being necessary for the connection or the separation. In particular, during connection and separation a user does not have to think about the correct sterile covering of non-sterile elements since the flaps are preferably held in or moved back into their closed position. For this, in particular, an elastically deformed element, such as a spring or a polymer block, can be used.

Further, it is advantageous when the endoscope has a first plug connector and when at least one end of the cable a second plug connector is provided that is complementary to the first plug connector and is connectable to the first plug connector of the endoscope. Preferably, with the aid of the first plug connector and of the second plug connector at least one optical fiber of the cable is couplable to at least one optical element of the endoscope. Alternatively or additionally, with the aid of the first plug connector and of the second plug connector at least one electric conductor of the cable is connectable to at least one electric connection of the endoscope. It is particularly advantageous when upon connection of the second plug connector of the cable to the first plug connector of the endoscope a disconnectable snap-in connection is established between the first plug connector and the second plug connector. As a result, for separating the second plug connector of the cable from the first plug connector of the endoscope only the snap-in connection has to be disconnected. Thus, an easy handling of the cable and of the endoscope is possible. The snap-in connection can in particular be configured such that for disconnecting the snap-in connection no tools are required but the snap-in connection is easily disconnectable by a manual operation.

Further, it is advantageous when the first sterile lock has a defined position with respect to a coupling interface of the endoscope during accommodation of the endoscope in the endoscope sheath, wherein the coupling interface of the endoscope comprises at least one electric connection of the endoscope or an optical element. As a result, it is achieved that by the defined position of the endoscope sheath with respect to the coupling interface of the endoscope, the cable or the plug connector connected to the cable can safely be connected to the endoscope.

Further, it is advantageous when the second sterile lock has a first connecting area to which the cable and/or the plug connector is connectable, and when the second sterile lock has a second connecting area to which a complementary connecting area of the first sterile lock is connectable. As a result, the plug connector or the cable can be connected in the second sterile lock independent of a connection of the first sterile lock to the second sterile lock. This facilitates the handling of the cable and makes the connection of the cable to the endoscope via the two sterile locks easier. Preferably, the first connecting area of the second sterile lock and the second connecting area of the second sterile lock are arranged on opposite sides of the second sterile lock. As a result, the connection of the cable or the plug connector to the first connecting area can be established independent of a connection between the first sterile lock and the second connecting area of the second sterile lock. Also, the second connecting area of the second sterile lock can be connected to the first sterile lock independent of whether the cable or the plug connector is connected to the second connecting area of the second sterile lock.

Here, it is advantageous when the first connecting area of the second sterile lock is connectable to the cable and/or the plug connector provided at the end of the cable via a first disconnectable snap-in connection and when the second connecting area of the second sterile lock is connectable to the connecting area of the first sterile lock via a second disconnectable snap-in connection. As a result, the connections between the sterile locks and between the second sterile lock and the plug connector or the second sterile lock and the cable are protected against unintended separation with the aid of the snap-in connection. On the other hand, if needed, they are separable by simply disconnecting the snap-in connection.

It is particularly advantageous when upon connection of the first sterile lock with the second sterile lock the first sterile flap automatically opens, and when upon connection of the first sterile lock with the second sterile lock the second sterile flap automatically opens, when the first sterile flap automatically closes upon separation of the first sterile lock from the second sterile lock, and when the second sterile flap automatically closes upon separation of the first sterile lock from the second sterile lock. As a result, it is guaranteed that no user operations are required for the sterile covering of non-sterile elements upon separation of the sterile locks from each other so that as a result it can be guaranteed to a large extent that the sterile area is not contaminated as a result of operator errors.

Here, it is particularly advantageous when upon connection of the first sterile lock to the second sterile lock an automatic unlocking of the first sterile flap takes place, when upon connection of the first sterile lock to the second sterile lock an automatic unlocking of the second sterile lock takes place, when upon separation of the first sterile lock from the second sterile lock an automatic locking of the first sterile flap takes place and when upon separation of the first sterile lock from the second sterile lock an automatic locking of the second sterile flap takes place. As a result, it is guaranteed that the flaps are locked in their closed position in the separated or non-connected state of the first sterile lock and the second sterile lock so that these cannot be opened by mistake: as a result, the risk of a contamination of the sterile area associated with an inadvertent opening is safely ruled out.

Further, it is advantageous when upon connection of the first sterile lock to the second sterile lock the sterile outside of the first sterile flap is arranged opposite to the sterile outside of the second sterile flap, when both the first sterile flap and the second sterile flap are open. The outside of the first sterile flap and the outside of the second connecting area face each other in the open state. As a result, it is reliably prevented that the insides of the connecting areas brought into contact with non-sterile elements upon handling of the sterile locks do not contaminate the sterile outsides of the other connecting areas so that a subsequent possible contamination of the sterile area by the otherwise contaminated outside of the connecting areas is ruled out.

Further, it is advantageous to accommodate in a portion of the endoscope sheath a shaft of an endoscope designed as a rod endoscope, and preferably to surround it. The endoscope sheath can comprise an optical element which is arranged opposite to the shaft end of the endoscope when the endoscope is accommodated in the endoscope sheath. In the simplest case, the optical element is configured as a light-permeable element not forming the light. Here, this can be a simple inspection glass. Alternatively, the optical element can be designed as a lens or prism.

When different optical elements are provided in different endoscope sheaths, the imaging of the light detected with the aid of the endoscope can be varied via the selection of the endoscope sheath so that the optical image capturing properties of the endoscope can be varied by the selection of the sheath.

A second aspect of the invention relates to an arrangement for the robot-assisted surgery. This arrangement is particularly suitable for a telerobot-assisted procedure within a sterile area. The arrangement comprises at least one arrangement according to claim 1 or a previously indicated development of the arrangement according to claim 1. Further, the arrangement comprises at least one manipulator having a manipulator arm. Further, the arrangement comprises at least one input device for the input of at least one input command. The endoscope accommodated in the endoscope sheath is connectable to the manipulator arm. The arrangement further comprises a control unit which positions the manipulator arm and the endoscope connected to the manipulator arm dependent on the input command with the aid of at least one drive unit. As a result, the manipulator arm changes the position of the endoscope in space preferably dependent on the input command. In this way, the position of the endoscope can easily be changed with the aid of a telemanipulator so that also during a surgery the direction of view and the position of the endoscope can easily be changed by user inputs via the input device with the aid of a telemanipulator system. Preferably, a surgical instrument that is connected to a further manipulator arm of the manipulator can be operated via the same input device and its position in space can be changed with the aid of the manipulator arm.

A third aspect of the invention relates to an arrangement for establishing and disconnecting a plug connection between a first non-sterile plug connector and a second non-sterile plug connector that is complementary to the first plug connector in a sterile environment. The arrangement comprises a first sterile sheath for accommodating the first plug connector and a second sterile sheath for accommodating at least the second plug connector. The first sheath comprises a first sterile lock which has at least one first sterile flap which in the closed state shields the first plug connector in a sterile manner. The second sheath comprises a second sterile lock which has at least one second sterile flap which in the closed state shields the second plug connector in a sterile manner. Upon connection of the first plug connector to the second plug connector a movement of the first sterile flap from its closed state into an open state takes place. Further, upon connection of the first plug connector to the second plug connector a movement of the second sterile flap from its closed state into an open state takes place so that a direct coupling of the first plug connector to the second plug connector is possible. When the first plug connector is separated from the second plug connector, a movement of the first sterile flap from the open state into the closed state as well as a movement of the second sterile flap from the open state into the closed state takes place so that, after separation, the first sterile flap at least shields the first plug connector in a sterile manner and the second sterile flap shields the second plug connector in a sterile manner.

By such an arrangement it is easily possible to shield non-sterile plug connectors in sterile manner so that they can be used without special care in a sterile environment. In addition, it is guaranteed that a direct connection between the plug connectors can be established in that upon connection of the plug connectors the respective sterile flaps of the first sterile lock and of the second sterile lock are opened. Further, it is guaranteed that after separation of the plug connectors these are again shielded in a sterile manner in that the sterile flaps of the sterile locks are closed again. Thus, a separation and a connection as well as a re-connection of the plug connectors in the sterile environment is possible without any problems so that, if necessary, this may also be done during a surgery.

Further, in all aspects or their developments it is advantageous when the first plug connector has at least one first electric contact element for establishing an electric connection, or at least one first optical element for establishing an optical connection, when the second plug connector has at least one second electric contact element for establishing a second electrical connection to the first contact element or at least one second optical element for establishing an optical connection to the optical element, when the at least one first electric contact and the at least one second electric contact and/or when the at least one first optical element and the at least one second optical element are arranged and configured such that when the first plug connector is connected to the second plug connector an electrical connection between the first contact element and the second contact element or an optical connection between the first optical element and the second optical element is established. The first plug connector and/or the second plug connector can be firmly connected to a medical device, in particular to the housing of a medical device. The medical device can in particular be an endoscope or a surgical instrument which can be used in particular together with a manipulator, preferably in the robot-assisted surgery.

Further, it is advantageous when the first plug connector and the second plug connector are designed symmetrically such that the electrical connection between the first contact element and the second contact element and/or the optical connection between the first optical element and the second optical element is possible both when the plug connectors are brought together in a first position and when the plug connectors are brought together in a second position, wherein in the second position one of the plug connectors has been rotated by 180° about an axis running perpendicularly to the contact plane of the plug connectors. Here, an easy intuitive connection is possible since in particular a connection of the plug connectors in two positions that are offset by 180 degrees is possible so that before bringing them together details of the plug connectors do not have to be taken into account but rather an intuitive bringing-together of the plug connectors is possible.

BRIEF DESCRIPTION OF THE DRAWINGS

Further features and advantages of the invention result from the following description which in connection with the enclosed Figures explains the invention in more detail on the basis of embodiments.

FIG. 7a shows a side view of a portion of the endoscope accommodated in the endoscope sheath and of the plug connector of the endoscope cable connected to the sterile adapter of the cable sheath in a first position before they are brought together;

FIG. 7b shows a sectional view of the arrangement according to FIG. 7a;

FIG. 8a shows the arrangement according to FIG. 7a in a second position when bringing together the plug connector of the endoscope cable with a plug connector of the endoscope;

FIG. 8b shows a sectional view of the arrangement according to FIG. 8a;

FIG. 9a shows the arrangement according to FIGS. 7a and 8a in a third position, in which the plug connector of the endoscope cable and the plug connector of the endoscope are brought closer together;

FIG. 9b shows a sectional view of the arrangement according to FIG. 9a;

FIG. 10b shows a sectional view of the arrangement according to FIG. 10a;

FIG. 11b shows a sectional view of the arrangement according to FIG. 11a;

FIG. 12b shows the exploded view according to FIG. 12a with the sterile flaps closed;

FIG. 15a shows a first perspective view of the cable sheath with the sterile adapter of the cable sheath;

FIG. 15b shows a second perspective view of the cable sheath with the sterile adapter of the cable sheath;

DETAILED DESCRIPTION

Figure 1:
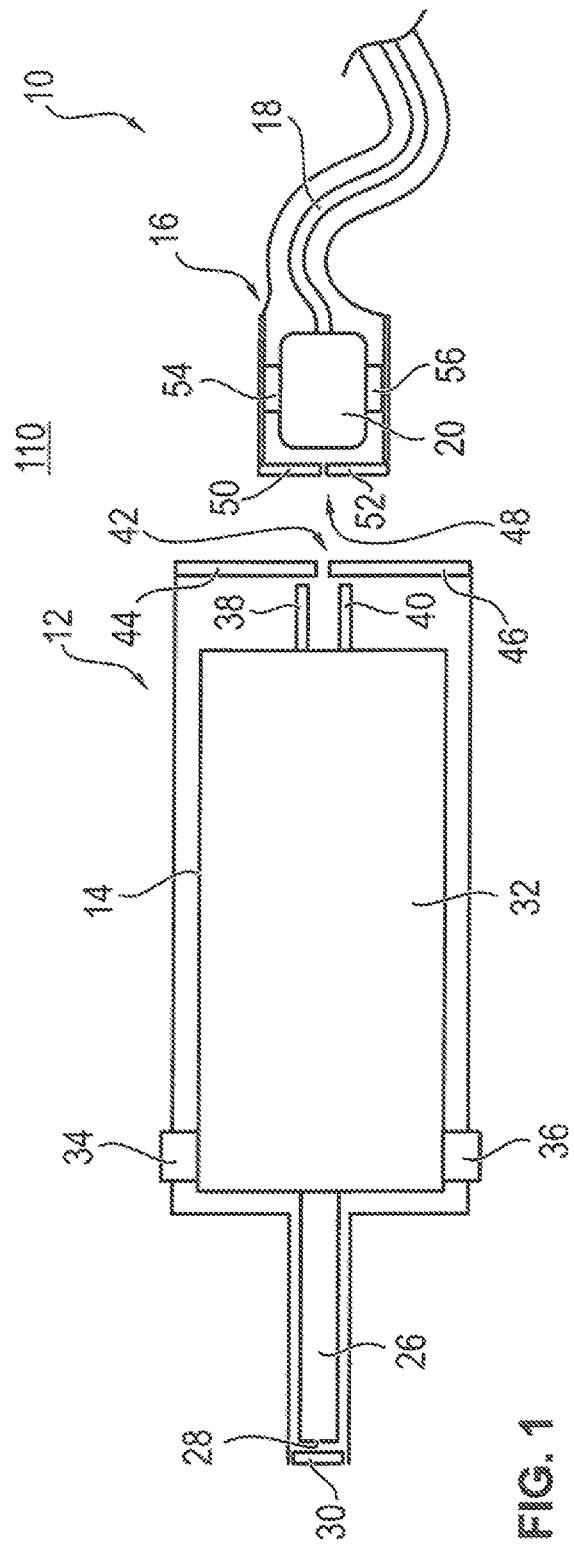
FIG. 1 shows a schematic sectional view of an arrangement with an endoscope accommodated in an endoscope sheath and an endoscope cable accommodated in a cable sheath in a non-connected state according to a first embodiment.

FIG. 1 shows a schematic sectional view of an arrangement 10 with an endoscope 14 accommodated in an endoscope sheath 12. The arrangement 10 further comprises an endoscope cable 18 surrounded by a cable sheath 16. The endoscope cable 18 serves to connect the endoscope 14 to a non-illustrated control unit for controlling the endoscope 14 and/or for processing the image data transmitted from the endoscope 14. At the endoscope-side end of the endoscope cable 18, a plug connector 20 is provided, with the aid of which the endoscope cable 18 is easily connectable to the endoscope 14 and again separable therefrom. The endoscope sheath 12 serves to shield the non-sterile endoscope 14 in a sterile area 110, i.e. a sterile environment, in a sterile manner. The cable sheath 16 serves to shield the non-sterile endoscope cable 18 and the plug connector 20 connected to the endoscope cable 18.

The endoscope 14 is a rod endoscope having a rod-shaped area 26 that can be inserted at least in part into a patient body and in which non-illustrated optical elements for guiding illumination light and for detecting and/or forwarding ambient light entering into the tip 28 of the rod-shaped area 26. An optical element is provided opposite to the tip 28 in the endoscope sheath 12, which element lets pass through at least a part of the illumination light to be emitted and lets pass through at least a part of the ambient light to the tip 28 of the rod-shaped area 26. In the simplest case, the optical element is an inspection glass or a window. In other embodiments, the optical element can be a lens or a prism or a combination of several individual optical elements.

The endoscope 14 further comprises an endoscope body 32 which in particular comprises a light source for generating illumination light and a control unit for detecting and processing images captured with the aid of an image sensor or for processing the image data generated during image capturing. In the present embodiment, mechanical connecting elements 34, 36 are provided, by which the endoscope 14 is fixable in the endoscope sheath 12. In the present case, the mechanical connecting elements 34, 36 are formed by a gauge ring integrated in the endoscope sheath 12. In other embodiments, also other mechanical connecting elements, such as screws, clamping or snap-in elements, may be provided. Alternatively or additionally, the endoscope sheath 12 can be formed such that it surrounds the overall endoscope 14 so tightly so that the endoscope 14 is fixed in its position relative to the endoscope sheath 12.

The endoscope 14 has at least one electric contact 38 for establishing an electrical connection between the endoscope 14 and at least one electric line of the endoscope cable 18. With the aid of this electric contact 38 in particular electrical energy can be transmitted to the endoscope 14 in order to provide in particular a control unit arranged in the endoscope 14 with electrical energy and/or to provide a light source present in the endoscope 14 with electrical energy. Alternatively or additionally, data, in particular image data, can be transmitted from the endoscope 14 via the endoscope cable 18 to an external control and/or processing unit via the electric contact 38 or via further electric contacts. Alternatively or additionally, data can also be transmitted from such an external control unit to the endoscope 14 in order to particularly control the function of the endoscope 14, for example the brightness or the spectrum of the illumination light or to activate for example a zoom function of the endoscope 14. In addition, the endoscope 14 comprises an optical connecting element 40 that is connected to a complementary optical connecting element of the plug connector 20 for optical data transmission, for the transmission of illumination light or for the transmission of optical image information from the endoscope to an external control and/or evaluation unit via the endoscope cable 18.

The endoscope sheath 12 comprises a first sterile lock 42 with a first sterile flap pair having the sterile flaps 44, 46. With the aid of the sterile flaps 44, 46, the contact area of the endoscope 14 with the electric contact 38 and the optical connecting element 40 is shielded in a sterile manner. The cable sheath 16 of the endoscope cable 18 comprises a second sterile lock 48 with the sterile flaps 50, 52, wherein the plug connector 20 of the endoscope cable 18 is connected to the housing of the sterile lock 48 with the aid of mechanical connecting elements 54, 56 so that the plug connector 20 is fixed in its position relative to the sterile flaps 50, 52 in the sterile lock 48. With the aid of the sterile flaps 50, 52 of the sterile lock 48, the non-sterile plug connector 20 is shielded from the sterile area 110. In FIG. 1, the plug connector 20 and the endoscope 14 are shown in a separated state, in which both the sterile flaps 44, 46 of the first sterile lock 42 and the sterile flaps 50, 52 of the second sterile lock 48 are closed.

Figure 2:
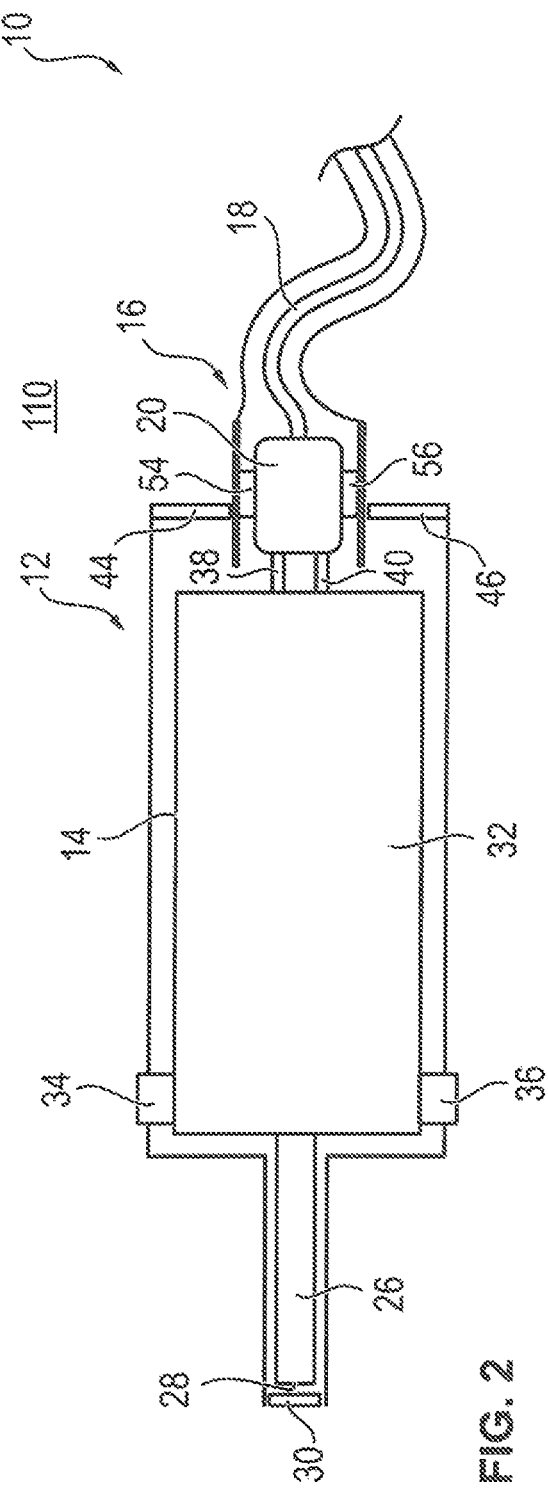
FIG. 2 shows the arrangement according to FIG. 1, wherein the endoscope and the endoscope cable are illustrated in a connected state.

FIG. 2 shows the arrangement according to FIG. 1, wherein the endoscope 14 with the endoscope cable 18 is illustrated in a connected state. Starting from the position illustrated in FIG. 1, the endoscope 14 present in the endoscope sheath 12 and the endoscope cable 18 present in the endoscope sheath 16 have been moved toward one another, until they have reached the state illustrated in FIG. 2. While being moved toward one another, the first sterile lock 42 of the endoscope sheath 12 and the second sterile lock 48 of the cable sheath 16 come into contact with one another. In doing so, both the lock flaps 44, 46 of the first sterile lock 42 and the lock flaps 50, 52 of the second sterile lock 48 are unlocked and opened. As a result, a direct connection between the electric contact 38 and the optical connecting element 40 and correspondingly complementary connecting elements or contact elements of the plug connector 20 is possible. This direct connection is automatically established when the plug connector 20 of the endoscope cable 18 and the endoscope 16 are moved closer to each other after the opening of the lock flaps 44, 46, 52, 54. Preferably, the electric contact element 38 and the optical connecting element 40 form part of a plug connector provided on the endoscope 14, which plug connector is complementary to the plug connector 20 of the endoscope cable 18. As a result, an easy and safe electrical and/or optical connection is possible between the endoscope 14 and the endoscope cable 18.

For separating the endoscope cable 18 arranged in the cable sheath 16 from the endoscope 14 arranged in the endoscope sheath 12 these are moved apart from one another, wherein both the lock flaps 44, 46 of the first sterile lock 42 and the lock flaps 50, 52 of the second sterile lock 48 are again automatically closed and locked so that after separation the arrangement 10 is again in the state shown in FIG. 1. Thus, the sterile area 110 was protected prior to the connection, during the connection, during the separation as well as after the separation against a contamination by the non-sterile elements of the endoscope 14 and of the cable 18 by the sterile endoscope sheath 12 with the first sterile lock 42 and by the sterile cable sheath 16 with the second sterile lock 48.

In the previously described manner, the endoscope cable 16 arranged in the cable sheath 18 can arbitrarily often be connected in the sterile area 110 to the endoscope 14 arranged in the endoscope sheath 12 or alternatively to a further endoscope arranged in a sterile endoscope sheath as well as again be separated therefrom without there being a risk that the sterile area 110 is contaminated.

Figure 3:
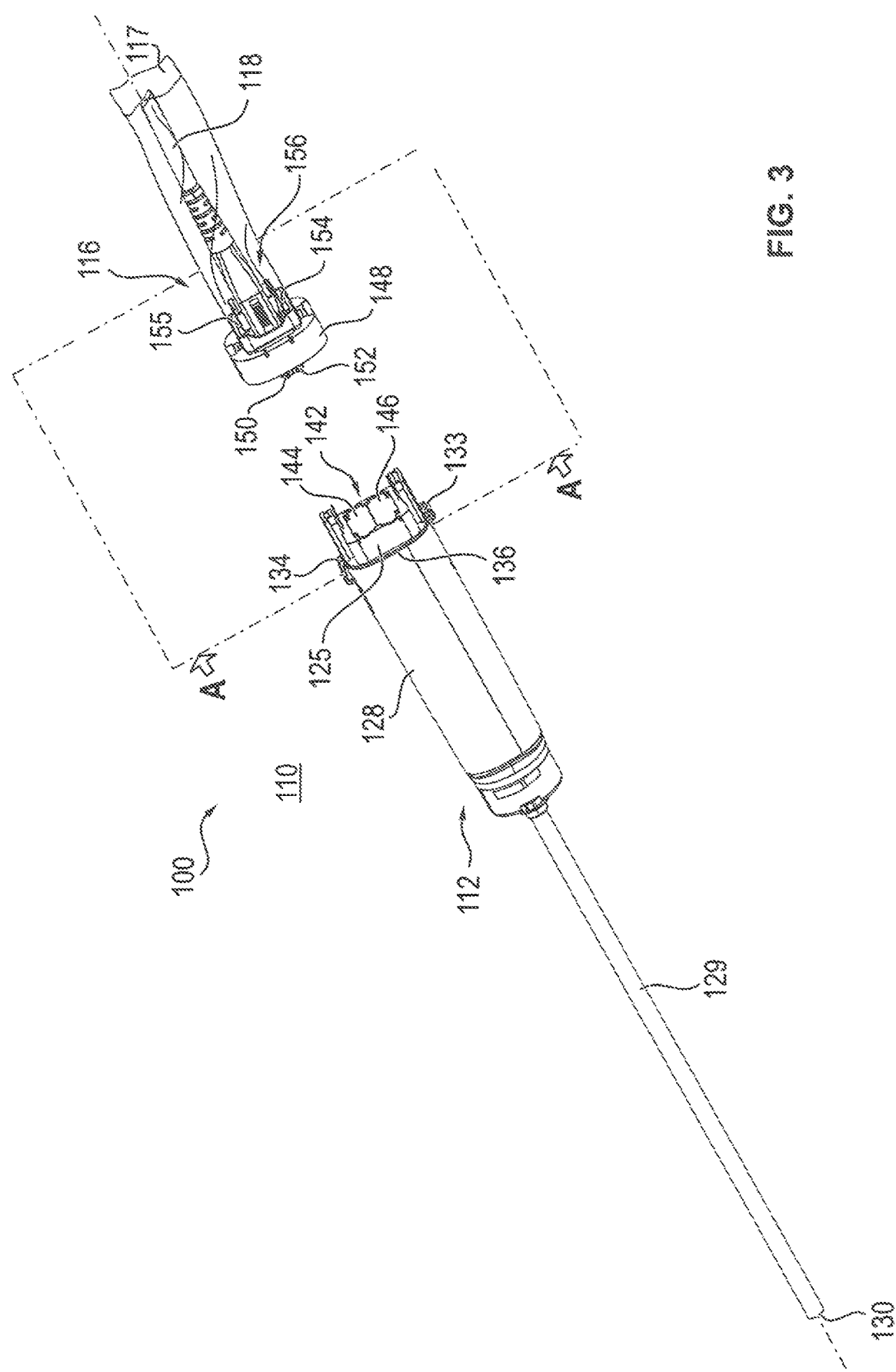
FIG. 3 shows an arrangement with an endoscope accommodated in an endoscope sheath and a plug connector of an endoscope cable connected to a sterile adapter, in which a disconnectable connection between endoscope cable and endoscope can be established, according to a second embodiment.

FIG. 3 shows an arrangement 100 with an endoscope accommodated in an endoscope sheath 112. The endoscope accommodated in the endoscope sheath 112 is not visible in FIG. 3. Further, the arrangement 100 comprises a sterile sheath 116 for surrounding an endoscope cable 118. The sterile sheath 116 comprises a sterile adapter 148. On its end provided for a connection to the endoscope accommodated in the endoscope sheath 112 the endoscope cable 118 has a plug connector 156 which is disconnectably connected to the sterile adapter 148 via a snap-in connector 154. In the arrangement 100 according to FIG. 3, a disconnectable connection between the endoscope cable 118 accommodated in the cable sheath 116 and the endoscope accommodated in the endoscope sheath 112 can be established. The non-sterile endoscope present in the endoscope sheath 112 and the endoscope cable 118 arranged in the cable sheath 116 are present in a sterile area 110, such as an operating room. The endoscope is shielded from the sterile area 110 by the endoscope sheath 112, and the endoscope cable 118 is shielded therefrom by the cable sheath.

The endoscope sheath 112 comprises a front part 129 for accommodating an endoscope rod or endoscope tube insertable at least in part into a patient body. The front part 129 of the endoscope sheath 112 is closed with the aid of an optical element 130 at its distal end. The optical element 130 can comprise a lens, a prism or a disk having no influence on the course of the beams.

The endoscope sheath 112 further comprises a middle part 128 for accommodating an endoscope housing and a closing element 125 with a sterile lock 142 connected to the middle part 128 via a hinge 133. By the closing element 125, an insertion and removal opening 136 of the endoscope sheath 112 for inserting and removing an endoscope into and from the endoscope sheath 112, respectively, can be closed in a sterile manner. In the closed state, the closing element 125 is lockable with the aid of a snap-in connector 134 which is present on the side of the insertion and removal opening 136 of the endoscope sheath 112 opposite to the hinge 133. The sterile lock 142 provided in the closing element 125 has sterile flaps 144, 146. The endoscope housing arranged in the middle part 128 of the endoscope sheath 112 is also referred to as endoscope body, in which in particular a light source for generating illumination light and a control unit for detecting and processing images captured with the aid of the image sensor or for processing the image data generated during image capturing can be provided. Further, mechanical connecting elements can be provided by which the endoscope is fixable in the endoscope sheath 112. The mechanical connecting elements can, for example, be formed by a gauge ring integrated into the endoscope sheath 112. In other embodiments, also other mechanical connecting elements such as screws, clamping or snap-in elements, can be provided. Alternatively or additionally, the endoscope sheath 112 can be designed such that it surrounds the endoscope altogether so tightly so that the endoscope is fixed in its position relative to the endoscope sheath 112.

The sterile adapter 148 of the cable sheath 116 comprises the sterile flaps 150, 152 and is also referred to as sterile lock. In the closed state of the sterile flaps 144, 146, 150, 152 shown in FIG. 3, these are locked. When bringing the sterile adapter 148 and the sterile lock 142 together, the sterile flaps 144, 146, 150, 152 are automatically unlocked and opened.

Figure 4:
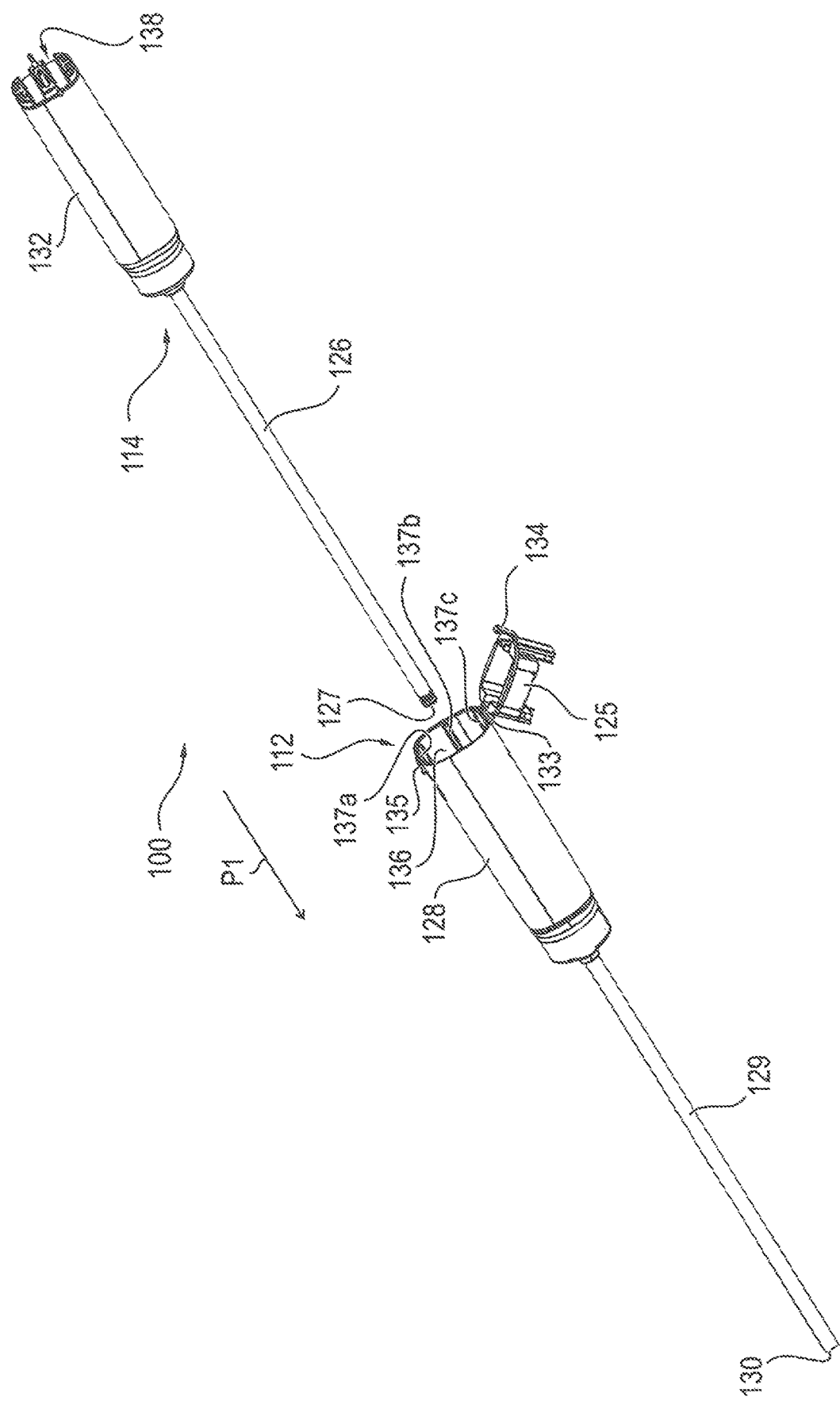
FIG. 4 shows the endoscope sheath and an endoscope that can be shielded in a sterile manner with the aid of the endoscope sheath, in a not yet connected state.

FIG. 4 shows the endoscope sheath 112 and an endoscope 114 that can be shielded in a sterile manner with the aid of the endoscope sheath 112 in a not yet connected state. For accommodating the endoscope 114 in the endoscope sheath 112, the endoscope 114 is inserted in the direction of the arrow P1 through the open insertion and removal opening 136 into the endoscope sheath 112. For this, the rod-shaped region 126 of the endoscope 114 is at first inserted into the insertion and removal opening 136 and then moved up into the front part 129 of the endoscope sheath 112 so that the tip 127 of the rod-shaped portion 126 of the endoscope 114 is arranged opposite to the optical element 130 of the endoscope sheath 112 present at the end of the front part 129. Upon insertion of the endoscope body 132 through the insertion and removal opening 136 into the middle part 128 of the endoscope sheath 112, the endoscope body 132 is guided by guiding webs 137a to 137f present inside in the middle part 128 of the endoscope sheath 112 and is held in a predetermined position in the middle part 128 of the endoscope sheath 112. At the end of the endoscope body 132 opposite to the rod-shaped portion 126, a hybrid plug connector 138 is arranged which comprises optical elements for the transmission of optical signals and/or illumination light and/or for the transmission of images. Further, the hybrid plug connector 138 comprises electric contacts for the transmission of electrical energy for supplying the endoscope 114 with electrical energy and/or for the transmission of signals and/or data from and to the endoscope 114. These data can in particular comprise image data generated on the basis of images captured by an image sensor present in the endoscope 114 and/or control data/control signals for controlling the endoscope 114. The hybrid plug connector 138 is complementary to the plug connector 156 of the endoscope cable 118 that is also designed as a hybrid plug connector, wherein the electric contacts and the optical elements of the plug connector 156 are complementary to the electric contacts and the optical elements of the plug connector 138.

Figure 5:
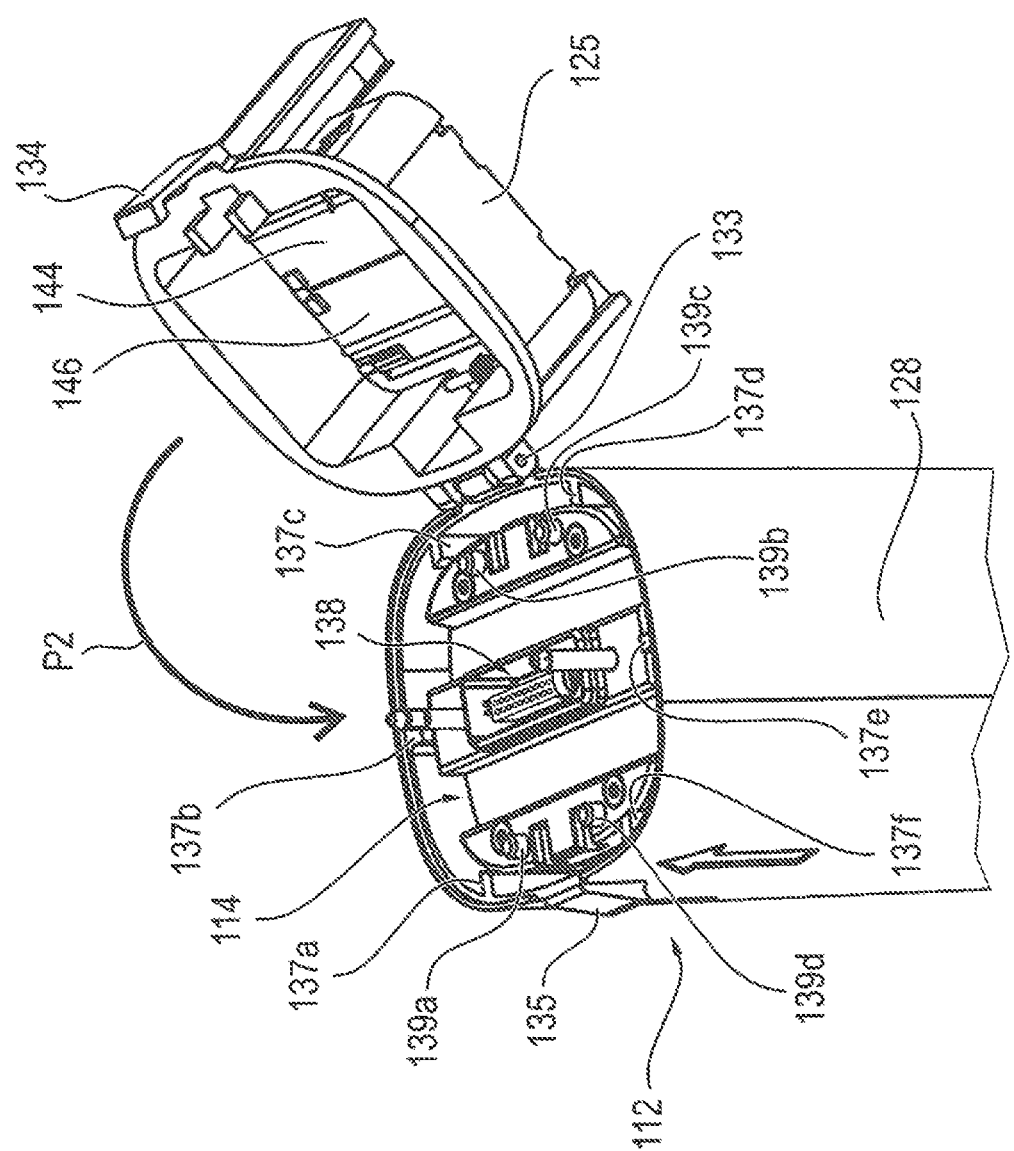
FIG. 5 shows a portion of the endoscope sheath with inserted endoscope with open insertion opening for inserting and removing the endoscope, wherein the endoscope sheath comprises a closing element for closing the insertion opening, into which closing element a first sterile lock is integrated.

FIG. 5 shows a portion of the endoscope sheath 112, wherein the endoscope 114 has been inserted into the endoscope sheath 112 and is present therein. The insertion and removal opening 136 is open in the arrangement illustrated in FIG. 5 and can be closed by the closing element 125 by pivoting the closing element 125 about the axis of rotation of the hinge 133 in the direction of the arrow P2. The snap-in connector 134 engages with an engagement element 135 formed on the middle part 128 of the endoscope sheath 112 when the insertion and removal opening 136 is closed by the closing element 125. As a result, the insertion and removal opening 136 is reliably closed in a sterile manner. The snap-in connector 134 can further in particular be actuated by an operator to release the engagement of the snap-in connector 134 with the engagement element 135 and to then pivot the closing element 125 about the axis of rotation of the hinge 133 opposite to the arrow P2. As a result, the insertion and removal opening 136 is again opened so that the endoscope 114 can again be removed from the endoscope sheath 112, for example after a surgery. At the opposite end of the tip 127 of the endoscope 114, several distance elements 139a to 139d are arranged in addition to the hybrid plug connector 138, which distance elements contact the closing element 125 in the closed state so that the endoscope 114 has a defined distance and thus a defined position relative to the sterile lock 142 of the closing element 125.

Figure 6:
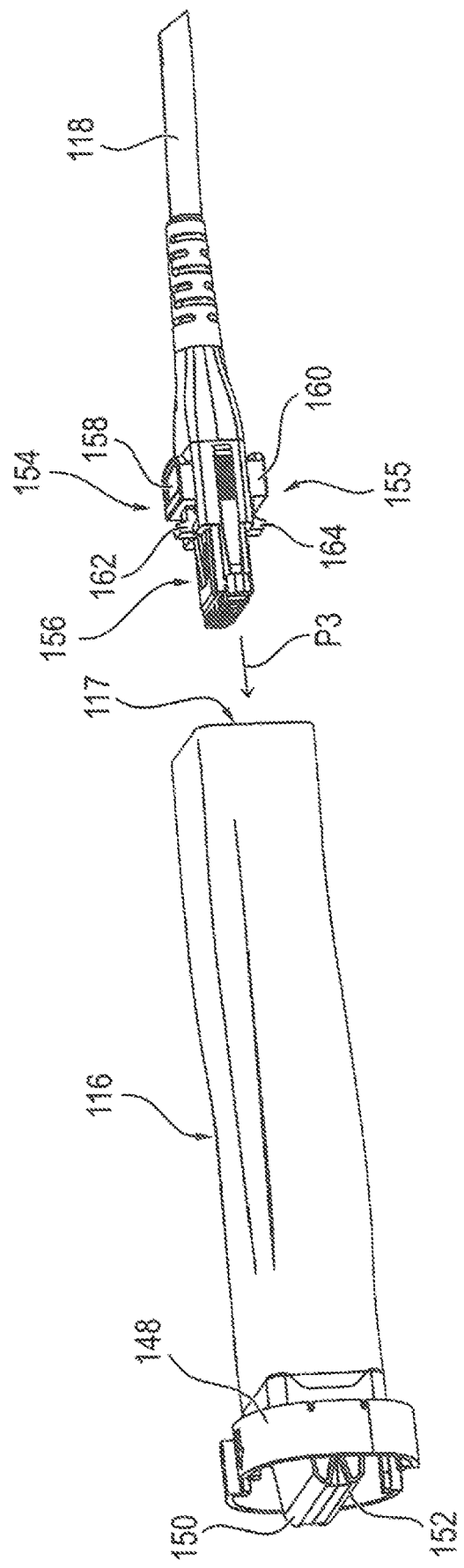
FIG. 6 shows the cable sheath for the sterile shielding of at least a part of the endoscope cable, wherein the cable sheath comprises a sterile adapter to which a plug connector provided at the end of the cable is connectable and that comprises a second sterile lock.

FIG. 6 shows the cable sheath 116 for the sterile shielding of at least a part of the endoscope cable 118. The cable sheath 116 comprises a connecting element designed as a sterile adapter 148, with which the plug connector 156 of the endoscope cable 118 is connectable via snap-in connectors 154, 155. In the present embodiment, the snap-in connectors 154, 155 are formed on the plug connector 156 of the endoscope cable 118 and are coupled with two actuating elements 158, 160, with the aid of which the snap-in elements 162, 164 are movable from the snap-in position shown in FIG. 6 into the release position in which the snap-in elements 162, 164 are no longer engaged with the complementary engagement elements of the sterile adapter 148 so that the plug connector 156 can again be disconnected from the sterile adapter 148.

For the sterile shielding of the cable 118 with the aid of the cable sheath 116 with respect to the sterile area 110, the plug connector 156 of the cable 118 is inserted into the open end 117 of the cable sheath 116 together with a portion of the cable 118. For this, the plug connector 156 is moved in the direction of the arrow P3 until the plug connector 156 contacts the sterile adapter 148 and until the snap-in elements 162, 164 of the snap-in connectors 154, 155 engage with the two complementary engagement elements of the sterile adapter 148 so that the plug connector 156 is firmly connected to the sterile adapter 148.

FIG. 7a shows a side view of a portion of the endoscope 114 accommodated in the endoscope sheath 112 and of the plug connector 156 of the endoscope cable 118 connected to the sterile adapter 148 of the cable sheath 116 in a first position prior to the connection of the plug connector 156 of the endoscope cable 118 with the plug connector 138 of the endoscope 114. FIG. 7b shows a sectional view of the arrangement according to FIG. 7a along the cutting plane A-A schematically illustrated in FIG. 3.

As can be seen in FIGS. 7a and 7b, the sterile flaps 150, 152 of the sterile adapter 148 are closed and shield the plug connector 156 with respect to the sterile area 110. Further, the sterile flaps 144, 146 of the sterile lock 142 of the closing element 125 of the sterile sheath 112 are closed and shield the plug connector 138 of the endoscope 114 with respect to the sterile area 110.

FIG. 8a shows the arrangement according to FIG. 7a in a second position when bringing together the plug connector 156 of the endoscope cable 118 and the plug connector 138 of the endoscope 114. FIG. 8b shows a sectional view of the arrangement according to FIG. 8a along the cutting plane A-A. When bringing together the sterile adapter 148 of the cable sheath 116, the sterile outsides of the sterile flaps 150, 152 contact the sterile outsides of the sterile flaps 144, 146 of the sterile lock 142 and begin to open them. Beforehand, locking elements for locking the sterile flaps 144, 146 have been unlocked via non-illustrated engagement elements so that the sterile flaps 144, 146 can be moved from their closed position into their open position. Both the closing element 125 of the endoscope sheath 112 and the sterile adapter 148 of the cable sheath 116 have guiding elements which are complementary to each other and are designed such that a connection of the plug connectors 138, 156 is only possible in the position shown in FIGS. 7a, 7b, 8a, 8b. By these guiding elements a bringing-together of the plug connectors 138, 156 in the described embodiment is only possible in a position in which the plug connectors 138, 156 are arranged exactly opposite so that the electric contact elements and optical elements of the plug connectors 138, 156 are positioned to each other accurately and, as a result thereof, are connectable easily by merely bringing together the endoscope cable 118 present in the cable sheath 116 and the endoscope 114 present in the endoscope sheath 112, as this will still be shown and explained in more detail in connection with FIGS. 9a to 11b.

FIG. 9a shows the arrangement according to FIGS. 7a and 8a in a third position, in which the plug connector 156 of the endoscope cable 118 and the plug connector 138 of the endoscope 114 have been moved closer together relative to their positions in FIGS. 7a, 7b, 8a, 8b. As can in particular be seen in FIG. 9b, the sterile flaps 144, 146 of the sterile lock 142 have been opened by their contact with the sterile flaps 150, 152 of the sterile adapter 148. In addition, the sterile flaps 150, 152 of the sterile adapter 148 have been moved by the contact with corresponding engagement elements of the closing element 125 and the bringing-together motion from the position shown in FIGS. 8a, 8b into the position shown in FIGS. 9a, 9b from their completely closed position into a somewhat opened position, which is illustrated in FIG. 9b. The plug connectors 138, 156 are still arranged opposite to each other and closer together in the position shown in FIGS. 9a, 9b as compared to the position shown in FIGS. 8a, 8b.

Figure 10B:
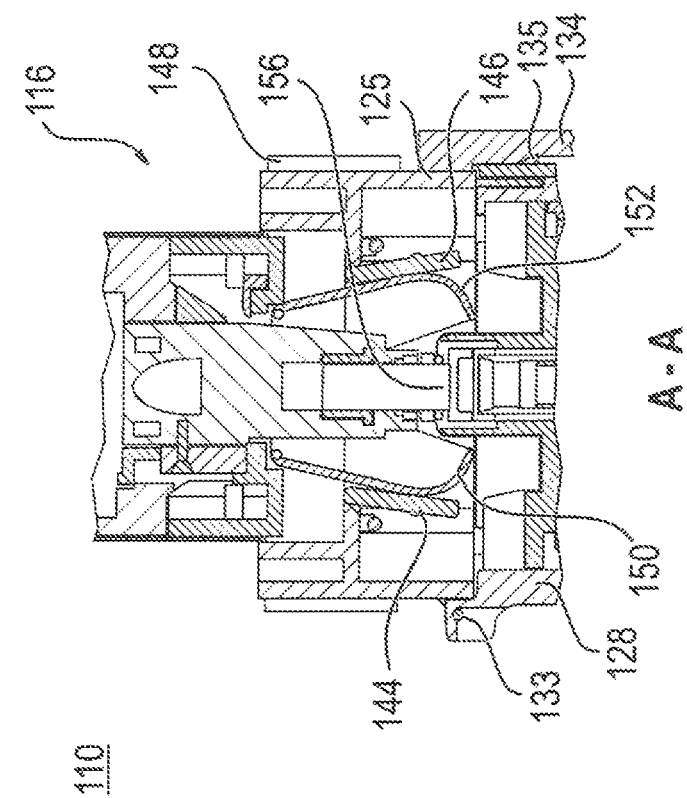
Figure 10A:
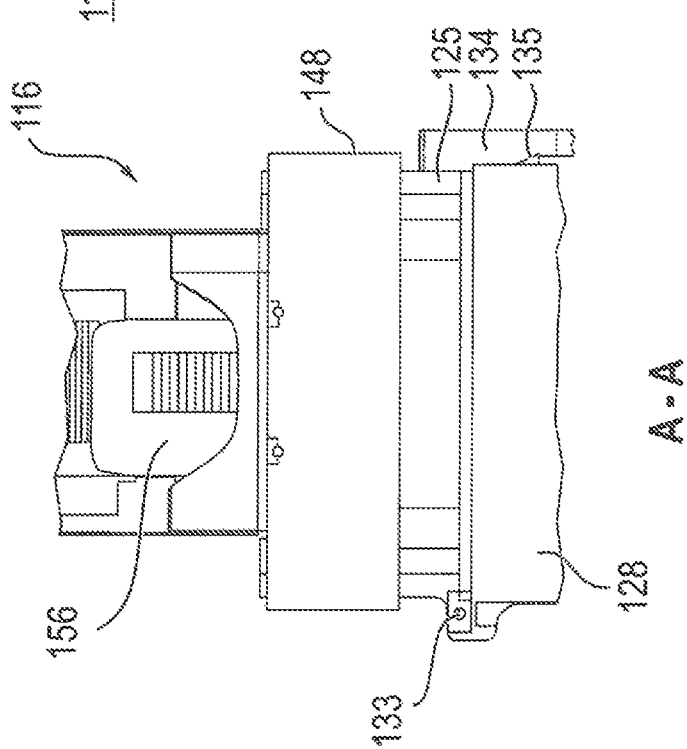
FIG. 10a shows the arrangement according to FIGS. 7a, 8a, 9a in a further position in which the plug connector of the endoscope cable and the plug connector of the endoscope are brought closer together and the coupling elements for establishing an optical connection between the endoscope cable and the endoscope are positioned with the aid of guiding means.
Figure 11B:
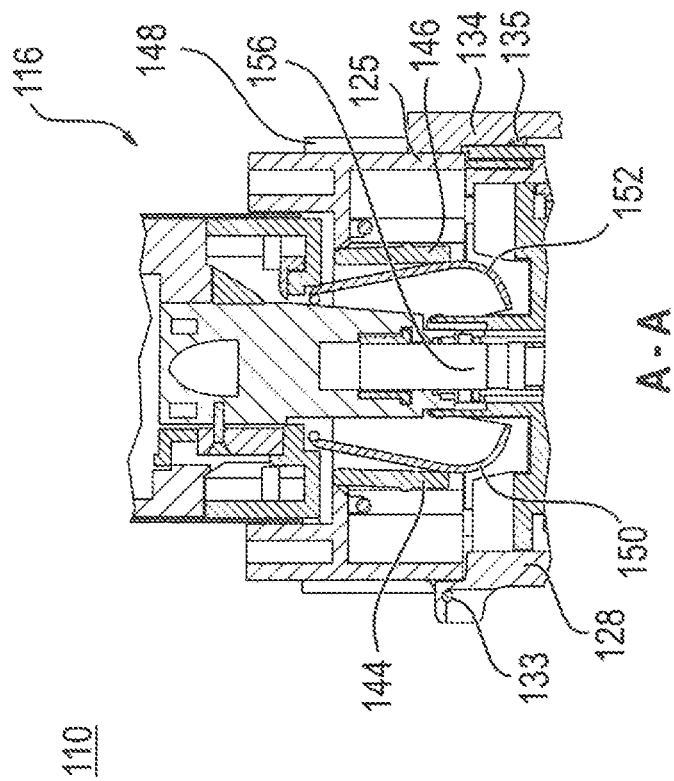
Figure 11A:
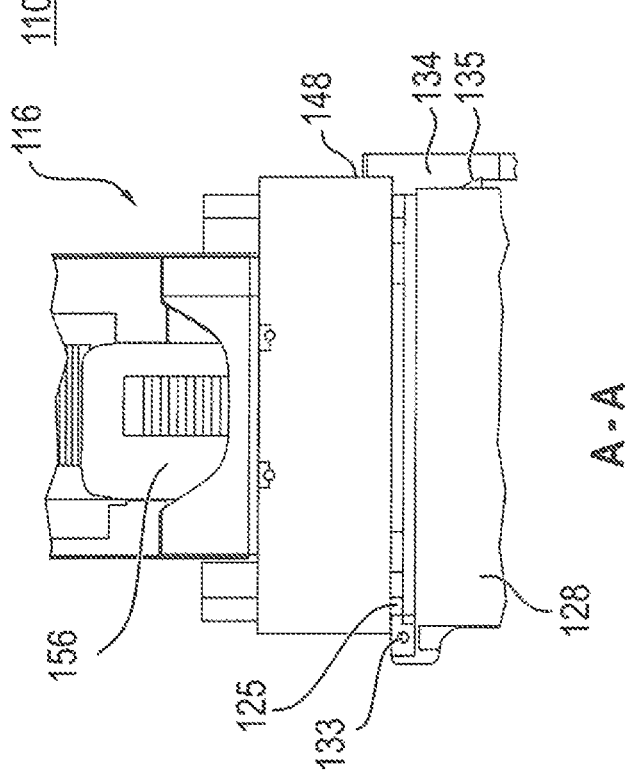
FIG. 11a shows the arrangement according to FIGS. 7a to 10a in a position in which the plug connector of the endoscope cable and the plug connector of the endoscope are arranged in a connected state.

FIG. 10a shows the arrangement according to FIGS. 7a, 8a and 9a in a further position in which the plug connector 156 of the endoscope cable 118 and the plug connector 138 of the endoscope 114 are even closer together and the optical transmission elements of the plug connectors 138, 156 for establishing an optical connection between the endoscope cable 118 and the endoscope 114 as well as the electric contact elements are arranged opposite to each other such that the plug connectors 138, 156 directly contact each other in case of a further movement in the direction of the arrow P4 so that the optical transmission elements are arranged in a suitable transmission position relative to each other and the electric contact elements contact each other, as shown in FIGS. 11a and 11b. In the position shown in FIGS. 10a and 10b, both the sterile flaps 144, 146 of the sterile lock 142 and the sterile flaps 150, 152 of the sterile adapter 148 are completely open, wherein in this position the housings of the plug connectors 138, 156 already contact each other. Upon a further movement of the sterile adapter 148 together with the plug connector 156 in the direction of the arrow P4, the plug connectors 138, 156 are brought into a correctly connected state, as shown in FIG. 11a and FIG. 11b. Via the engagement elements for opening the sterile flaps 150, 152, these are again slightly closed upon a movement from the position shown in FIG. 10a, 10b into the position shown in FIG. 11a 11b, wherein the closing of the sterile flaps 150, 152, 144, 146 is effected by the spring force of a spring engaged with one of the sterile flaps 144, 146, 150, 152. The springs are biased upon opening of the respective sterile flap 144, 146, 150, 152 and, upon closing of the respective sterile flap 144, 146, 150, 152, they are released.

When the plug connectors 138, 156 are separated, these are moved from their position shown in FIGS. 11a, 11b into their position shown in FIGS. 7a, 7b. Here, a movement of the sterile adapter 148 in a direction opposite to the arrow P4 takes place, wherein both the sterile flaps 144, 146 of the sterile lock 142 and the sterile flaps 150, 152 of the sterile adapter 148 are automatically closed and locked in the closed state. Thus, the non-sterile plug connectors 138, 156 are again covered in a sterile manner also after the separation of the cable 118 from the endoscope 114 so that a contamination of the sterile area 110 is effectively prevented.

Figure 12A:
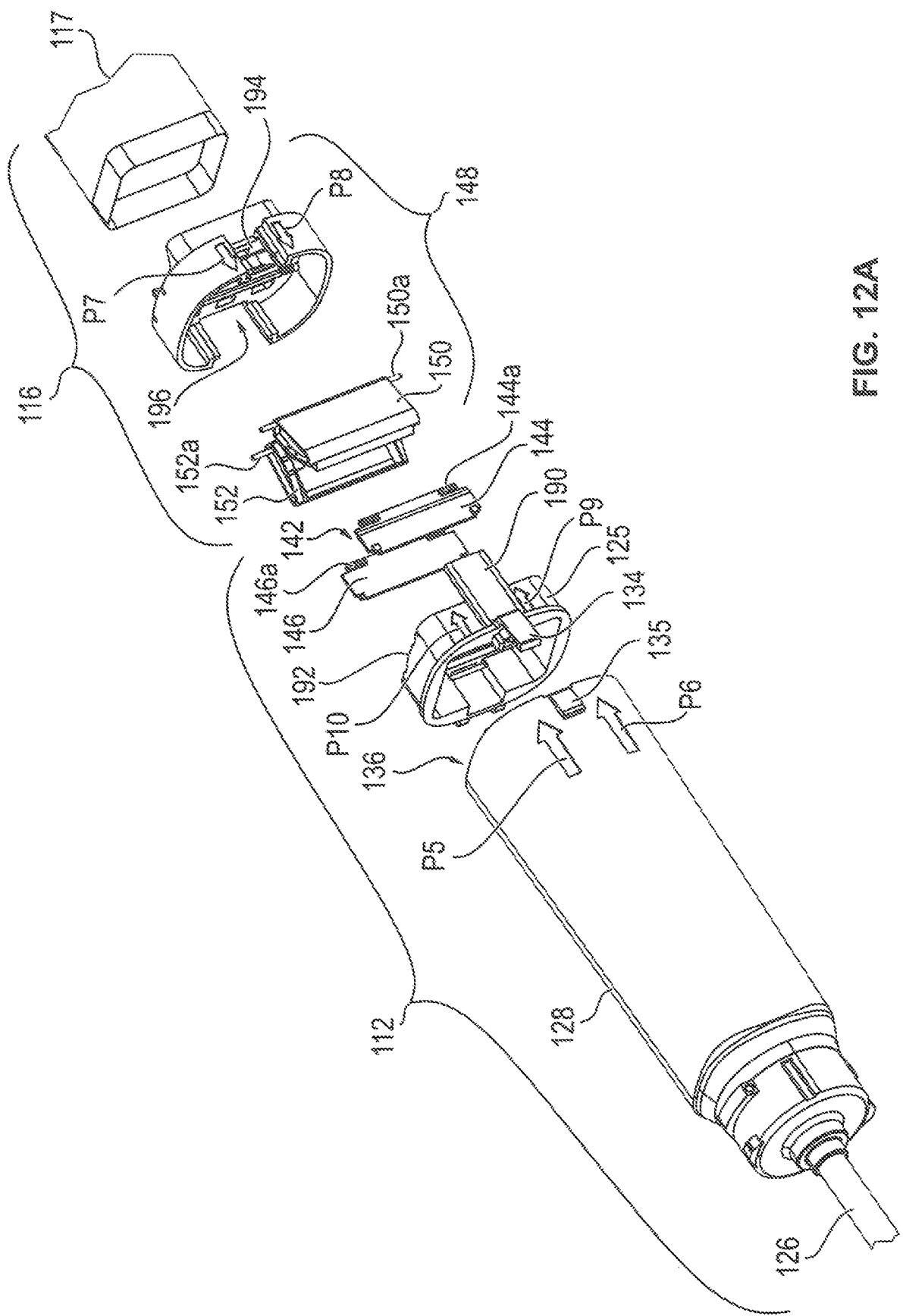
FIG. 12a shows an exploded view of the elements of the endoscope sheath and of the elements of the cable sheath with the sterile flaps open.

FIG. 12a shows an exploded view of the elements of the endoscope sheath 112 and the elements of the cable sheath 116 with the sterile flaps 144, 146, 150, 152 open. Both on the circumferential surface of the middle part 128 of the endoscope sheath 112 and on the sterile adapter 148 and the closing element 125 arrows P5 to P10 visible from outside are provided, which give the operator a hint how the cable sheath 116 with the sterile adapter 148 is to be brought together with the closing element 125 of the endoscope sheath 112 so that a connection is established between the endoscope cable 118 and the endoscope 114, as this has previously been explained in connection with FIGS. 7a to 11b. For a rotatable mounting, the sterile flaps 144, 146, 150, 152 each have connecting pins 144a, 146a, 150a, 152a, with the aid of which the respective sterile flap 144, 146, 150, 152 is rotatably mounted about the longitudinal axis of the respective pin 144a, 146a, 150a, 152a in corresponding recesses of the closing element 125 and the sterile lock 148, respectively, so that they can be pivoted about the respective axis of rotation from a closed into an open position and vice versa. In FIG. 12a, the sterile flaps 144, 146, 150, 152 are illustrated in their open position in which they are situated when the sterile adapter 148 is connected to the closing element 125. The closing element 125 further has two engagement elements 190, 192 which engage into corresponding recesses 194, 196 of the sterile adapter 148 when the sterile adapter 148 of the cable sheath 116 is connected to the closing element 125 of the endoscope sheath 112.

FIG. 12b shows the exploded view of FIG. 12a with closed sterile flaps. The sterile flaps 144, 146, 150, 152 are arranged in this position when the sterile adapter 148 is not connected to the closing element 125. In this closed position, the sterile flaps 144, 146, 150, 152 are locked with the aid of non-illustrated locking elements so that the sterile flaps 144, 146, 150, 152 cannot be opened inadvertently by a pressure on the sterile flaps 144, 146 or by the insertion of an object into the opening gap 165 between the sterile flaps 150, 152.

Figure 13:
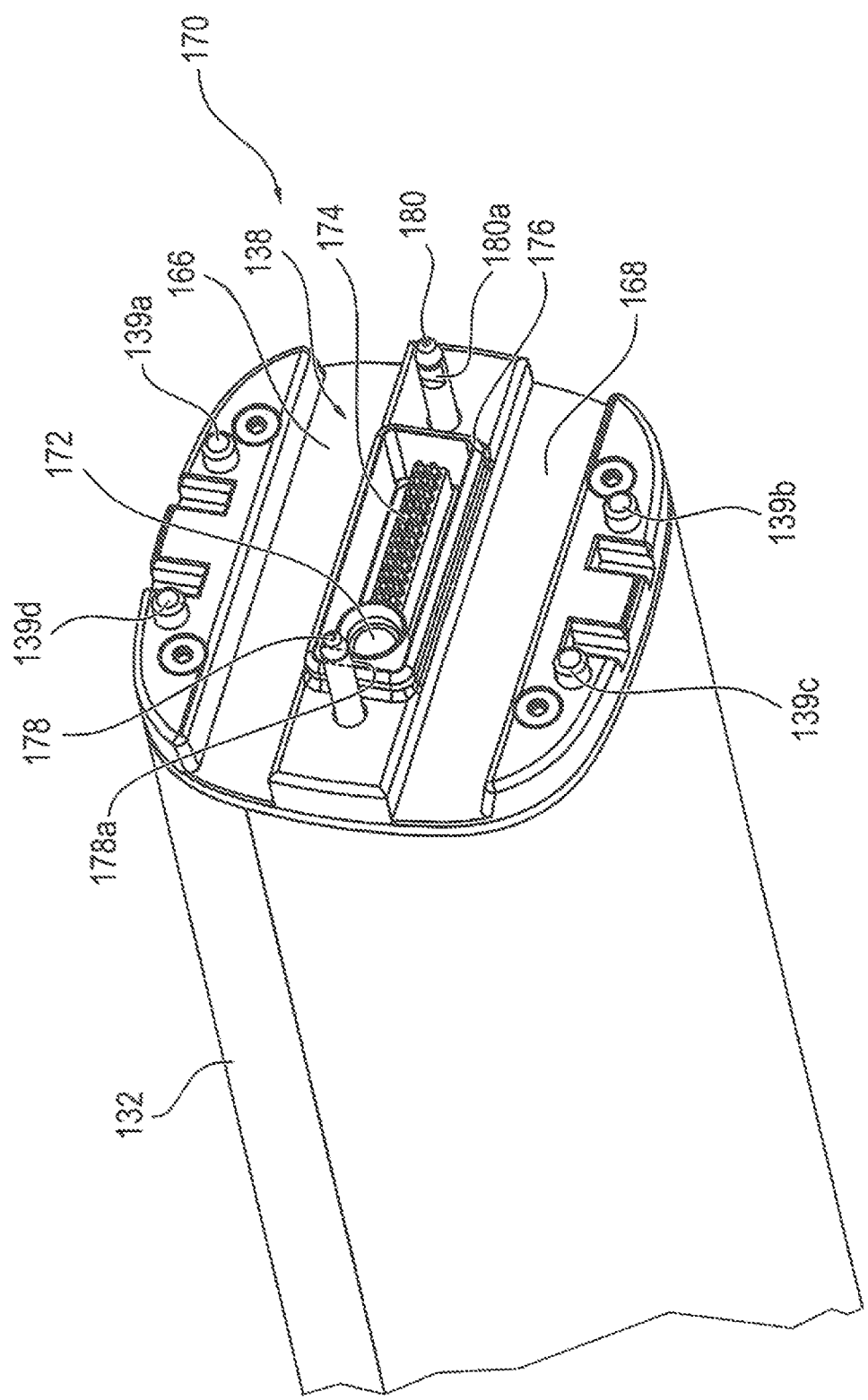
FIG. 13 shows a perspective view of a portion of the endoscope with the plug connector of the endoscope.

FIG. 13 shows a perspective view of a portion of the endoscope 114 with the plug connector 138. The plug connector 138 is arranged on the back of the endoscope 114, i.e. on the side of the endoscope 114 opposite to the rod-shaped area 126. This back is identified with the reference sign 170 in FIG. 13. On the back 170, two recesses 166, 168 are provided which are formed in strips and between which the plug connector 138 of the endoscope 114 is arranged. In the connected state, the front portions of the sterile flaps 150, 152 are situated in these recesses 166, 168, as can be seen in FIG. 11b. The plug connector 138 has an optical transmission channel 172 for the transmission of illumination light, surrounding light detected by the endoscope 114 and/or for the transmission of optical signals, in particular for data transmission. In addition, the plug connector 138 comprises in the present embodiment 24 contact elements, one of which being identified with the reference sign 174. In other embodiments, also more or less contact elements can be provided, in particular the contact elements can also have a different shape and/or size. With the aid of these contact elements, signals, data and/or electrical energy, for example, for supplying control units, image capturing units and/or illuminating units of the endoscope 114 can be transmitted. In the present embodiment, the contact elements 174 and the optical transmission channel 172 are arranged in a common plug connector housing 176. In the present embodiment, the housing 176 has a longitudinal shape, wherein the longitudinal sides of the housing 176 are oriented parallel to the longitudinal axes of the recess 166, 168. Further, the plug connector 138 comprises two guiding and locking pins 178, 180 arranged next to the housing 176. The guiding and locking pins 178, 180 each have at least one recess 178a, 180a, into which a complementary snap-in element of the plug connector 156 of the endoscope cable 118 can engage.

Figure 14:
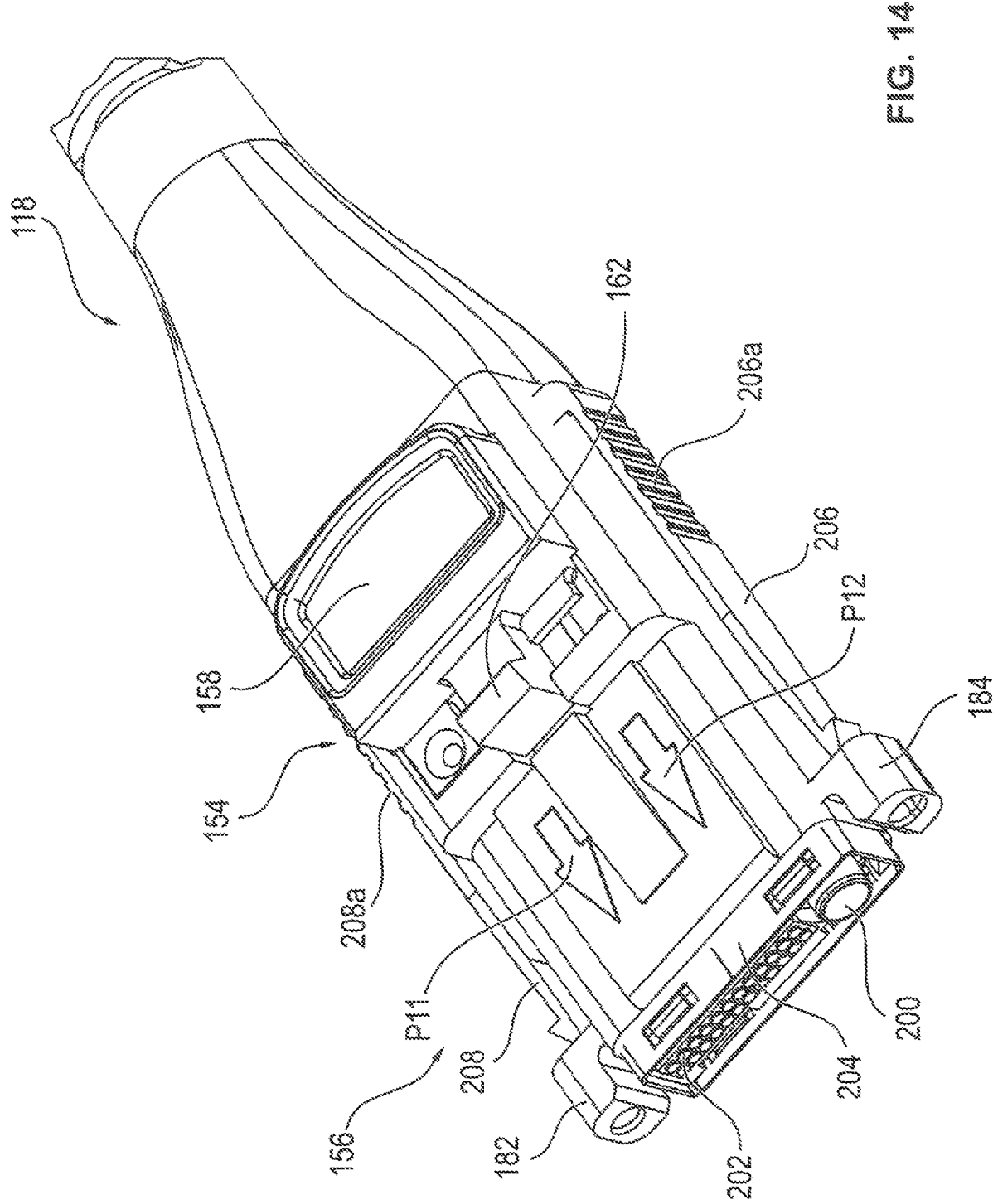
FIG. 14 shows a perspective view of a portion of the endoscope cable together with the plug connector arranged at the cable end.

FIG. 14 shows a perspective view of a portion of the endoscope cable 118 together with the plug connector 156 arranged at the end of the endoscope cable 118. As already explained in connection with FIG. 6, the snap-in connector 154, 155 with the actuating elements 158, 160 and the snap-in elements 162, 164 serves to connect the plug connector 156 in the sterile adapter 148. By actuating the actuating elements 158, 160, this snap-in connection can again be disconnected and the plug connector 156 be separated from the sterile adapter 148. The plug connector 156, also referred to as plug, has an optical transmission channel 200 which is compatible to the optical transmission channel 142 of the plug connector 138 of the endoscope 114. In addition, the plug connector 156 has 24 electric contact elements, one of which being identified with the reference sign 202, which are compatible to the electric contact elements 174 of the plug connector 138. Further, the plug connector 156 has a housing 204 that is insertable into the housing 176 of the plug connector 138 of the endoscope 114. In addition, the plug connector 156 has, next to the front sides of the longitudinal housing 204, one guiding bush 182, 184 each, through which in the connected state of the plug connectors 138, 156 the guiding and locking pins 178, 180 are passed so that one snap-in element 206, 208 engages into a respective recess 178a, 180a of the guiding ad locking pins 178, 180 and forms a snap-in connection. By pressing the actuating areas 206a, 208a of the snap-in elements 206, 208 a snap-in connection established between the guiding and locking pins 178, 180 and the snap-in elements 206, 208 can again be disconnected. The direction arrows P11, P12 indicate a direction to the user in which the plug connector 156 has to be moved for a connection to the plug connector 138 in order to bring these together or the direction in which the plug connector 156 has to be moved to connect it to the sterile adapter 148.

FIG. 15a shows a first perspective view of the cable sheath 116 with the sterile adapter 148 of the cable sheath 116. FIG. 15b shows a second perspective view of the cable sheath 116 with the sterile adapter 148. In FIGS. 15a, 15b, receiving openings 212 to 218 can be seen into which the guiding pins 150a, 152a of the sterile flap 150, 152 are inserted so that the sterile flaps 150, 152 are pivotable about the longitudinal axes of the pins 150a, 152a. To each sterile flap 144, 146, 150, 152 one spring is allocated, holding the respective sterile flap 144, 146, 150, 152 in its closed position, wherein the sterile flap 144, 146, 150, 152 can only be opened against the spring force of the spring. As a result, the spring moves the sterile flaps 144, 146, 150, 152 in its closed position when the sterile flap 144, 146, 150, 152 is open. In FIG. 15a, the spring of the sterile flap 152 is identified with the reference sign 152b. The sterile lock 148 further has two opposing engagement elements, of which in FIG. 15a one engagement element is visible and is identified with the reference sign 210. The snap-in elements 162, 164 of the plug connector 156 engage into these engagement elements 210 when the plug connector 156 is connected to the sterile adapter 148.

Figure 16:
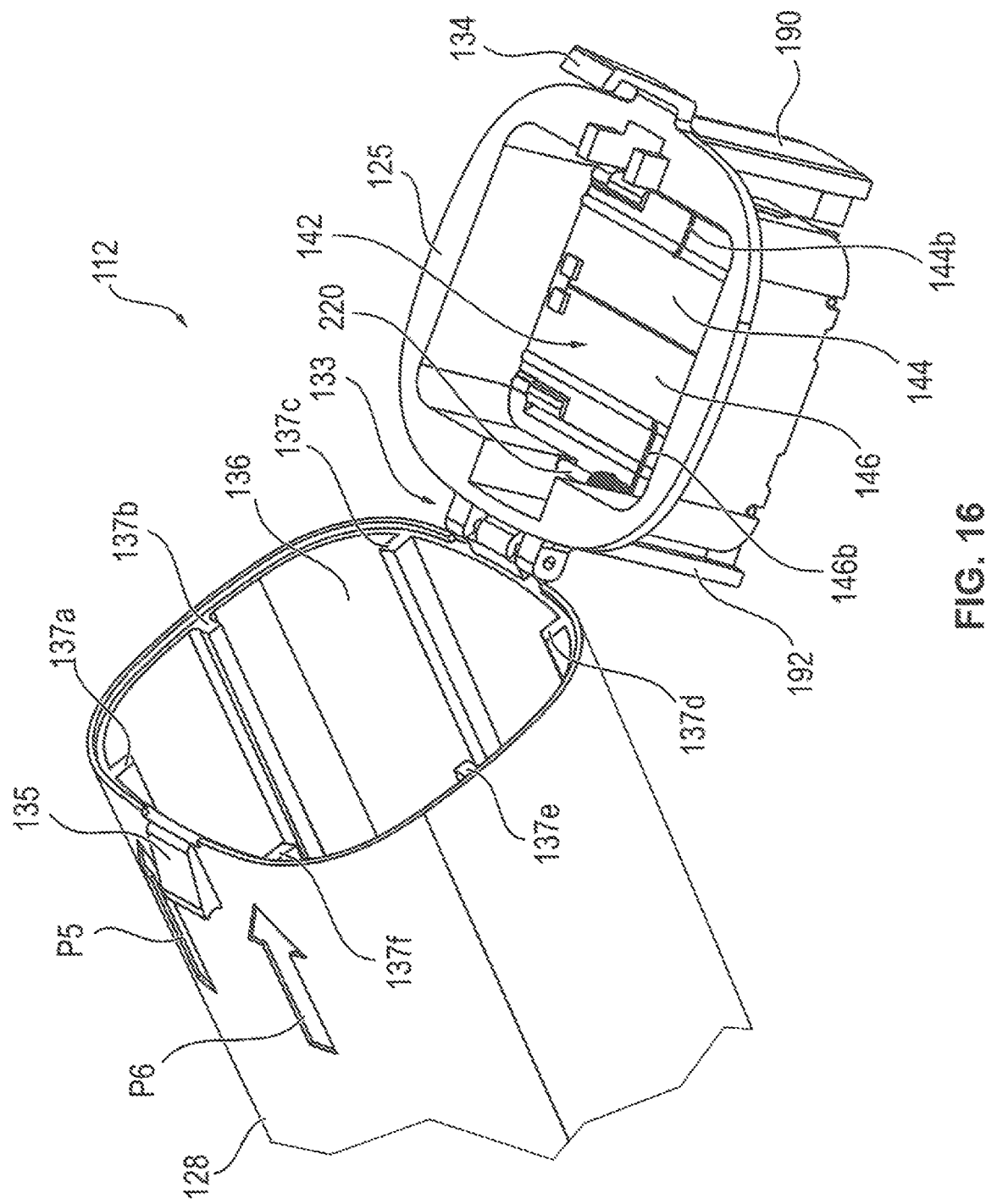
FIG. 16 shows the endoscope sheath and the closing element of the endoscope sheath in an open state.

FIG. 16 shows the endoscope sheath 112 and the closing element 125 of the endoscope sheath in an open state. In FIG. 16, the springs 144b, 146b of the sterile flaps 144, 146 are illustrated. As can be seen with spring 146b, this is a spiral spring which is arranged about a guiding pin 220, wherein the non-visible spring end is engaged with the closing element 125.

Figure 17:
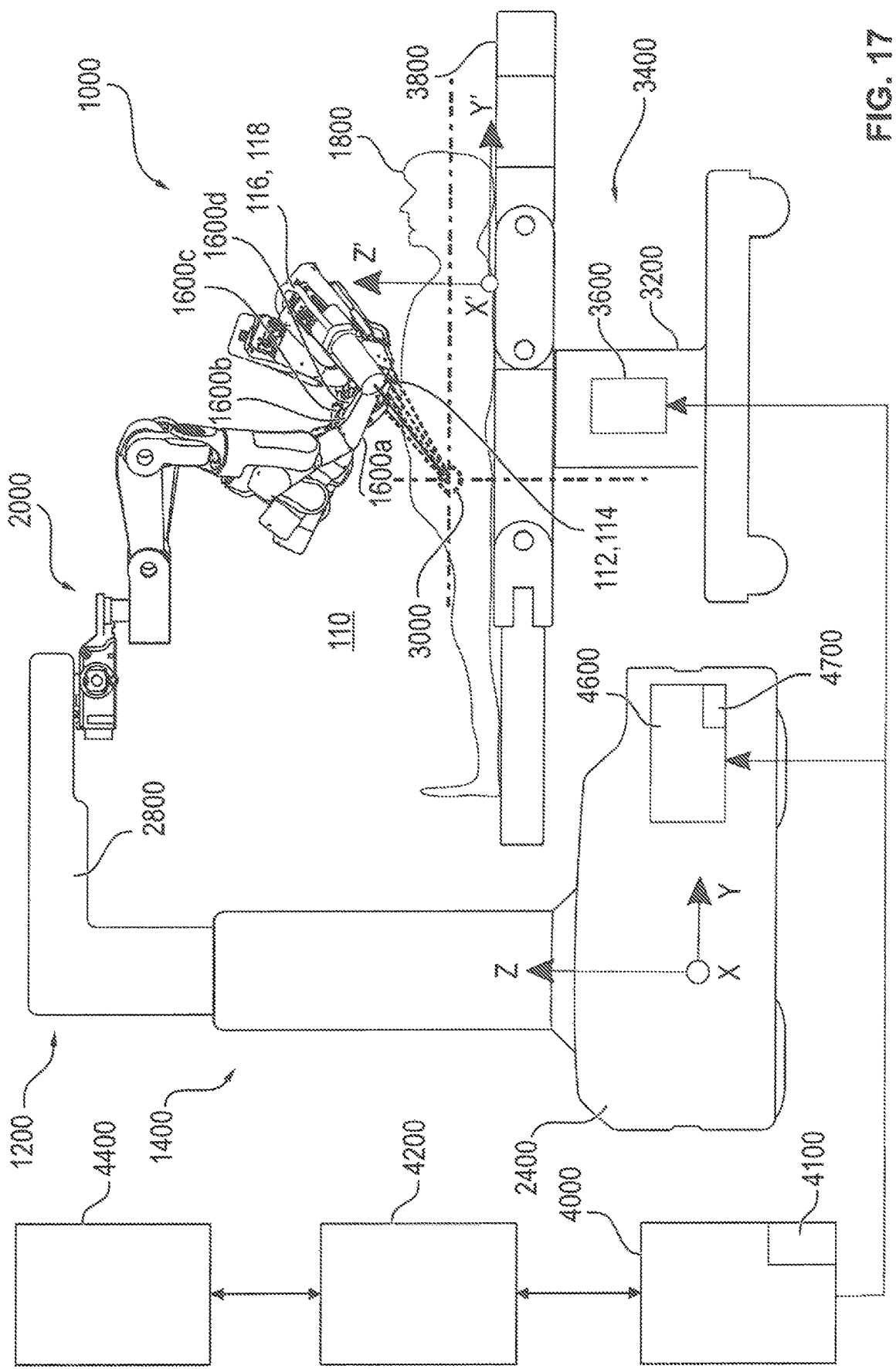
FIG. 17 shows a schematic side view of a system for the robot-assisted surgery with a manipulator having four manipulator arms to which one instrument unit each is connectable.

FIG. 17 shows a schematic side view of a system 1000 for the robot-assisted surgery with a manipulator 1200 having a stand 1400 and four manipulator arms 1600a to 1600d. The manipulator 1200 is generally also referred to as a device for the robot-assisted surgery. The system 1000 serves to perform a surgical intervention on a patient 1800 positioned on an operating table 3400. Based on the anatomy of the patient 1800 and the operation to be performed, the coordinates x'z, y'z, z'z of a target operation area 3000 in a patient coordinate system X', Y', Z' are determined and these coordinates x'z, y'z, z'z have been stored in a preset manner. The manipulator 1200 has a coordinate system X, Y, Z of the device 1200, the coordinate origin of which is arranged in a stand foot 2400 of a stand 1400 of the manipulator 1200. The stand 1400 has an L-shaped stand arm 2800, at the end of which that is remote from the stand foot 2400 the manipulator arms 1600a to 1600d are connected via a stand head 2000.

The operating table 3400 has an operating table column 3200 in which a control unit 3600 of the operating table 3400 is arranged and on which a patient support surface 3800 comprising several segments is arranged. The control unit 3600 serves to control the movement of elements of the operating table 3400, in particular for a length adjustment of the operating table column 3200 and thus for adjusting the height of the patient support surface 3800 and for adjusting individual segments as well as the inclination and the swing of the patient support surface 3800. Preferably, however, the adjustment of the segments of the operating table 3400 during a surgery by the manipulator 1200 is blocked. The system 1000 further comprises a control unit 4600 of the manipulator 1200 as well as a central control unit 4000 which is connected via data lines to the control unit 4600 of the manipulator 1200, the control unit 3600 of the operating table and an operating panel 4200 with a display unit 4400. The control unit 4000 has an output unit 4100 and the control unit 4600 has an output unit 4700, via each of which optical and/or acoustical signals can be output.

Figure 18:
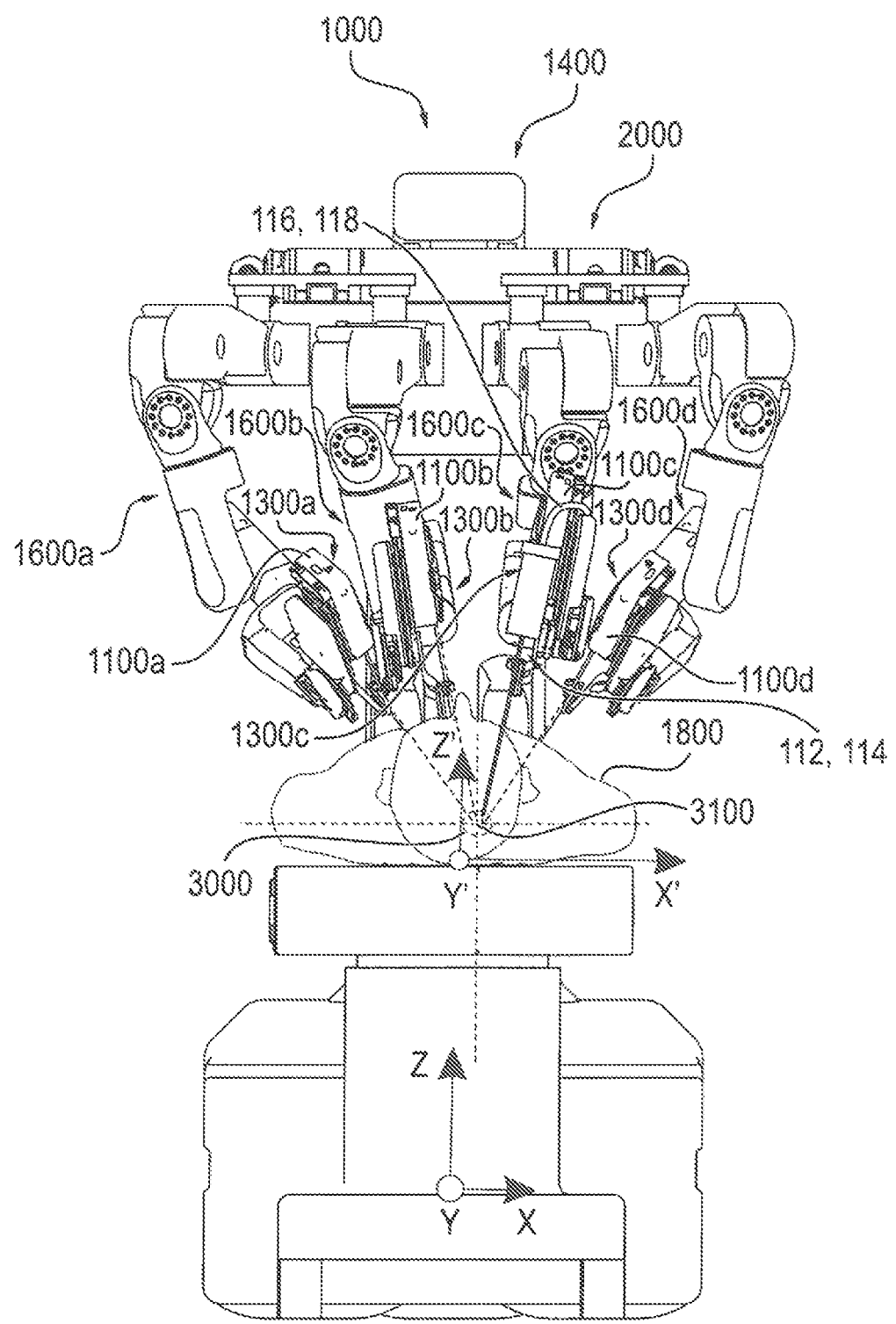
FIG. 18 shows a schematic front view of the system according to FIG. 17.

FIG. 18 shows a schematic front view of the system 1000 according to FIG. 17. At the proximal end of the manipulator arms 1600a to 1600d, one coupling unit 1100a to 1100d each is arranged to which one instrument unit 1300a to 1300d for performing the surgery is connected each time. The instrument shafts of the respective surgical instrument of the instrument units 1300a to 1300d are indicated by broken lines.

In the illustrated embodiment, the instrument unit 1300c is the rod endoscope 114 accommodated in the endoscope sheath 112 and connected to the control unit 4100 via the cable 118 accommodated in the cable sheath 116. In the present embodiment, the other instrument units 1300a, 1300b and 1300d are instrument units with end effectors, in particular for performing the surgery with the aid of the system 1000. In other embodiments, also two endoscopes and two surgical instruments can be connected with the manipulator arms 1600a to 1600d. In other embodiments, also more or less manipulator arms 1600a to 1600d may be provided or only some of the available manipulator arms 1600a to 1600d will be used for a surgery.

What is claimed is:

1. An arrangement for the sterile handling of a non-sterile endoscope in a sterile environment, the arrangement having a sterile endoscope sheath for accommodating the endoscope, a cable that is connectable to the endoscope, and a sterile cable sheath for accommodating at least a portion of the cable, wherein
the endoscope sheath comprises a first sterile lock having at least one first sterile flap which in a closed state to shields the non-sterile endoscope arranged in the endoscope sheath in a sterile manner,
and the cable sheath comprises a second sterile lock having a second sterile flap which in the closed state is configured to shields one of the cable or a plug connector present on the cable in a sterile manner,
such that when the one of cable or the plug connector is connected to the endoscope, movement of the first sterile flap from the closed state into an open state and a movement of the second sterile flap from the closed state into an open state takes place so that a direct coupling of the cable to the endoscope or of the plug connector to a complementary plug connector of the endoscope is possible, and
such that when the cable is separated from the endoscope, movement of the first sterile flap from the open state into the closed state and a movement of the second sterile flap from the open into the closed state takes place so that the first sterile flap shields the endoscope arranged in the endoscope sheath in a sterile manner after separation and the second sterile flap shields the cable arranged in the one of cable sheath or the plug connector in a sterile manner after separation and
wherein the first sterile eflap and the second sterile flap automatically open when the first sterile lock is connected to the second sterile lock, and the first sterile flap and the second sterile flap automatically close when the first sterile lock is separated from the second sterile lock.

2. The arrangement according to claim 1, wherein the second sterile lock is connectable to the cable or to the plug connector present on the cable via a disconnectable snap-in connection.

3. The arrangement according to claim 1, wherein the endoscope sheath has an opening into which the endoscope is insertable, and the opening of the endoscope sheath is closable in a sterile manner with the aid of a closing element, the closing element comprising the first sterile lock.

4. The arrangement according to claim 1, wherein the cable is an electric cable with at least one electric conductor, an optical cable, a light guide cable or a hybrid cable with at least one electric conductor and at least one optical fiber,
and the plug connector of the cable couples the at least one optical fiber of the cable with at least one optical element of the endoscope and/or the plug connector connects the at least one electric conductor of the cable to the at least one electric connection of the endoscope.

5. The arrangement according to claim 1, wherein the endoscope has a first plug connector, a second plug connector complementary to the first plug connector provided at least one end of the cable, which is connectable to the first plug connector of the endoscope, and with the aid of the first plug connector and of the second plug connector at least one optical fiber of the cable is couplable with at least one optical element of the endoscope and/or with the aid of the first plug connector or the second plug connector at least one electric conductor of the cable is connectable to at least one electric connection of the endoscope.

6. The arrangement according to claim 5, wherein when the second plug connector of the cable is connected to the first plug connector of the endoscope, a disconnectable snap-in connection is established between the first plug connector and the second plug connector; and
for separating the second plug connector of the cable from the first plug connector of the endoscope at least the snap-in connection has to be disconnected.

7. The arrangement according to claim 1, wherein the first sterile lock has a defined position relative to a coupling interface of the endoscope when the endoscope is accommodated in the endoscope sheath, and the coupling interface of the endoscope comprises at least one electric connection of the endoscope or an optical element.

8. The arrangement according to claim 1, wherein the second sterile lock has a first connecting area comprising an engagement element and a connector on one side of the second sterile lock and a second connecting area comprising an engagement element and a connector on an opposing side of the second sterile lock.

9. The arrangement according to claim 8, wherein the connector in the first connecting area is a snap-in connector connectable to the cable and/or to the plug connector provided at the end of the cable, and the connector in the second connecting area of the second sterile lock is a snap-in connector connectable to a complementary connecting area of the first sterile lock.

10. The arrangement according to claim 1, wherein when the first sterile lock is connected to the second sterile lock an automatic unlocking of the first sterile flap is performed,
that when the first sterile lock is connected to the second sterile lock an automatic unlocking of the second sterile flap is performed,
that when the first sterile lock is separated from the second sterile lock an automatic locking of the first sterile flap is performed, and
that when the first sterile lock is separated from the second sterile lock an automatic locking of the second sterile flap is performed.

11. The arrangement according to claim 1, wherein a sterile outside of the first sterile flap is arranged opposite to a sterile outside of the second sterile flap when the first sterile lock is connected to the second sterile lock, and when both the first sterile flap and the second sterile flap are open, the sterile outside of the first sterile flap and the sterile outside of the second sterile flap face each other in the open state.

12. The arrangement according to claim 1, wherein a portion of the endoscope sheath accommodates and preferably surrounds a shaft of an endoscope formed as a rod endoscope, and the endoscope sheath comprises an optical element that is arranged opposite to the shaft end of the endoscope when the endoscope is accommodated in the endoscope sheath.

13. A system for the robot-assisted surgery, in particular for a telerobot-assisted procedure within a sterile area,
with the arrangement according to claim 1,
with at least one manipulator having a manipulator arm,
with at least one input device for the input of at least one input command,
characterized in that the endoscope accommodated in the endoscope sheath is connected to the manipulator arm,
that the system comprises a control unit that positions the manipulator arm and the endoscope connected to the manipulator arm dependent on the input command with the aid of at least one drive unit.

14. An arrangement for establishing and disconnecting a plug connection between a first non-sterile plug connector and a second non-sterile plug connector complementary to the first plug connector in a sterile surrounding, the arrangement having
a first sterile sheath for accommodating at least the first plug connector, and a second sterile sheath for accommodating at least the second plug connector,
the first sheath comprises a first sterile lock which has at least one first sterile flap which in the closed state shields the first plug connector in a sterile manner,
the second sheath comprises a second sterile lock having at least one second sterile flap which in the closed state shields the second plug connector in a sterile manner,
such that when the first plug connector is connected to the second plug connector a movement of the first sterile flap from the closed state into an open state and a movement of the second sterile flap from the closed state into an open state takes place so that a direct coupling of the first plug connector to the second plug connector is possible, and
such that when the first plug connector is separated from the second plug connector a movement of the first sterile flap from the open state into the closed state and a movement of the second sterile flap from the open state into the closed state takes place so that the first sterile flap shields at least the first plug connector in a sterile manner after separation and the second sterile flap shields the second plug connector in a sterile manner after separation, and
wherein the first sterile flap and the second sterile flap automatically open when the first sterile lock is connected to the second sterile lock, and the first sterile flap and the second sterile flap automatically close when the first sterile lock is separated from the second sterile lock.

15. The arrangement according to claim 14, wherein the first plug connector has at least one first electric contact element for establishing an electric connection or at least one first optical element for establishing an optical connection,
and the second plug connector has at least one second electric contact element for establishing an electric connection with the first electric contact element or at least one second optical element for establishing an optical connection with the first optical element,
and the at least one first electric contact element and the at least one second electric contact element and/or that the at least one first optical element and the at least one second optical element are arranged and formed such that when the first plug connector is connected to the second plug connector an electrical connection between the first electric contact element and the second electric contact element or an optical connection between the first optical element and the second optical element is established.

16. The arrangement according to claim 14, wherein the first plug connector and the second plug connector are symmetrically formed such that the electrical connection between the first electric contact element and the second electric contact element and/or the optical connection between the first optical element and the second optical element is possible both when bringing together the plug connectors in a first position and when bringing together the plug connectors in a second position, in which one of the plug connectors has been rotated by 180° about an axis extending perpendicular to the contact plane of the plug connectors.

* * * * *

UNITED STATES PATENT AND TRADEMARK OFFICE
CERTIFICATE OF CORRECTION

PATENT NO. : 11,547,282 B2
APPLICATION NO. : 16/303740
DATED : January 10, 2023
INVENTOR(S) : Fabian Weise, Martin Luck and Hartmut Vogelsang It is certified that error appears in the above-identified patent and that said Letters Patent is hereby corrected as shown below:

In the Claims

Column 17, Claim 1, Line 61-62:
"at least one first sterile flap which in a closed state to shields"
Should be:
"at least one first sterile flap which in a closed state is configured to shield"

Column 17, Claim 1, Line 66:
"configured to shields"
Should be:
"configured to shield"

Column 18, Claim 1, Line 2:
"movement"
Should be:
"a movement"

Column 18, Claim 1, Line 11:
"movement"
Should be:
"a movement"

Column 18, Claim 1, Line 19:
"sterile eflap"
Should be:
"sterile flap"

Signed and Sealed this
Thirteenth Day of June, 2023

*Katherine Kelly Vidal*

Katherine Kelly Vidal
*Director of the United States Patent and Trademark Office*

Column 19, Claim 14, Line 62:
"at least the second plug connector,"
Should be:
"at least the second plug connector, wherein"